United States Patent
Rigneault et al.

(10) Patent No.: US 11,947,101 B2
(45) Date of Patent: Apr. 2, 2024

(54) DEVICES AND METHODS FOR TRANSPORTING AND CONTROLLING LIGHT BEAMS

(71) Applicants: Centre National de la Recherche Scientifique, Paris (FR); Université d'Aix-Marseille, Marseilles (FR); Université de Lille, Lille (FR); Ecole Centrale de Marseille, Marseilles (FR)

(72) Inventors: Hervé Rigneault, Allauch (FR); Géraud Bouwmans, Cysoing (FR); Esben Andresen, Lille (FR); Siddarth Sivankutty, Marseilles (FR); Viktor Tsvirkun, Marseilles (FR); Olivier Vanvincq, Dunkirk (FR)

(73) Assignees: Centre National de la Recherche Scientifique, Paris (FR); Université d'Aix-Marseille, Marseilles (FR); Université de Lille, Lille (FR); Ecole Centrale de Marseille, Marseilles (FR)

(*) Notice: Subject to any disclaimer, the term of this patent is extended or adjusted under 35 U.S.C. 154(b) by 588 days.

(21) Appl. No.: 17/278,026
(22) PCT Filed: Sep. 10, 2019
(86) PCT No.: PCT/EP2019/074142
§ 371 (c)(1),
(2) Date: Mar. 19, 2021
(87) PCT Pub. No.: WO2020/058043
PCT Pub. Date: Mar. 26, 2020

(65) Prior Publication Data
US 2021/0382290 A1    Dec. 9, 2021

(30) Foreign Application Priority Data
Sep. 20, 2018   (FR) ..................... 1858545

(51) Int. Cl.
G02B 23/24   (2006.01)
A61B 1/00    (2006.01)
G02B 23/26   (2006.01)

(52) U.S. Cl.
CPC ...... *G02B 23/2469* (2013.01); *A61B 1/00167* (2013.01); *A61B 1/00172* (2013.01); *G02B 23/26* (2013.01)

(58) Field of Classification Search
CPC .................. G02B 6/02042; G02B 6/06; G02B 2006/0209; G02B 23/2469;
(Continued)

(56) References Cited

U.S. PATENT DOCUMENTS 8,585,587 B2 * 11/2013 French ................. A61B 5/0071
                                                       600/181
10,571,678 B2    2/2020 Andresen et al.
(Continued)

FOREIGN PATENT DOCUMENTS

JP    2018-502638 A    2/2018
WO    2017/191685 A1   11/2017

OTHER PUBLICATIONS

E. R. Andresen et al. "Two-photon lensless endoscope" Optics Express vol. 21, No. 18; Aug. 27, 2013; 20713-20721 (9 pages).
(Continued)

*Primary Examiner* — William J Carter
(74) *Attorney, Agent, or Firm* — Osha Bergman Watanabe & Burton LLP

(57) ABSTRACT

According to one aspect, the invention relates to a device (200) for transporting and controlling light beams comprising a light guide (40) comprising a bundle (50) of uncoupled single-mode optical fibers ($F_i$), each single-mode optical fiber ($F_i$) being intended to receive an elementary light beam ($B_{1i}$) at a proximal end and to emit a light beam ($B_{2i}$) at a distal end, said bundle of single-mode optical fibers comprising, in operation, a minimum radius of curvature corresponding to a maximum curvature of the bundle of fibers. The device (200) furthermore comprises an optical device
(Continued)

for phase controlling, said device being arranged on the side of the proximal end of the light guide (40) and comprising at least a first spatial light modulator (30) suitable for applying a phase shift to each of the elementary beams ($B_{1i}$), and a control unit (60) for controlling the first spatial light modulator, said unit being configured to apply a phase shift to each of the elementary beams ($B_{1i}$) so as to form, at the distal end of the light guide, an illumination beam with a predefined phase function. According to the present description, said bundle (50) of single-mode optical fibers is twisted, and comprises a twist period (P) defined to preserve said phase function at the distal end of the light guide when the bundle of single-mode optical fibers is subjected to a curvature lower than said maximum curvature.

14 Claims, 18 Drawing Sheets

(58) Field of Classification Search
CPC .............. G02B 6/02085; G02B 6/4401; G02B 6/4413; G02B 23/26; G02B 23/24
See application file for complete search history.

(56) References Cited

U.S. PATENT DOCUMENTS

| | | | | |
|---|---|---|---|---|
| 2002/0088931 | A1* | 7/2002 | Danisch | G01D 5/35383 250/227.14 |
| 2017/0299806 | A1* | 10/2017 | Kopp | G02B 6/02085 |
| 2017/0371069 | A1* | 12/2017 | Malling | G01V 1/226 |
| 2019/0072378 | A1 | 3/2019 | Hane | |

OTHER PUBLICATIONS

E. R. Andresen et al. "Toward endoscopes with no distal optics: video-rate scanning microscopy through a fiber bundle" Optical Society of America; Optics Letters vol. 38, No. 5; Mar. 1, 2013 (3 pages).
E. R. Andresen et al. "Measurement and compensation of residual group delay in a multi-core fiber for lensless endoscopy" Journal of the Optical Society of America B vol. 32, No. 6; Jun. 2015; 1221-1228 (8 pages).
T. Cizmár et al. "Exploiting multimode waveguides for pure fibre-based imaging" Nature Communications; Aug. 28, 2012 (9 pages).
M. Napiorkowski et al. "Rigorous simulations of a helical core fiber by the use of transformation optics formalism" Optics Express vol. 22, No. 19; Sep. 15, 2014 (13 pages).
P. St. J. Russell et al. "Helically twisted photonic crystal fibres" Philisophical Transactions A, vol. 375; Sep. 19, 2016 (18 pages).
Office Action issued in Japanese Patent Application No. 2021-515582 dated May 9, 2023 (10 pages).
International Search Report for corresponding International Application No. PCT/EP2019/074142, dated Dec. 6, 2019 (15 pages).
Written Opinion for corresponding International Application No. PCT/EP2019/074142, dated Dec. 6, 2019 (5 pages).
V. Tsvirkun; "Bending-induced inter-core group delays in multicore fibers"; Optics Express, vol. 25, No. 25; Dec. 11, 2017 (13 pages).

* cited by examiner

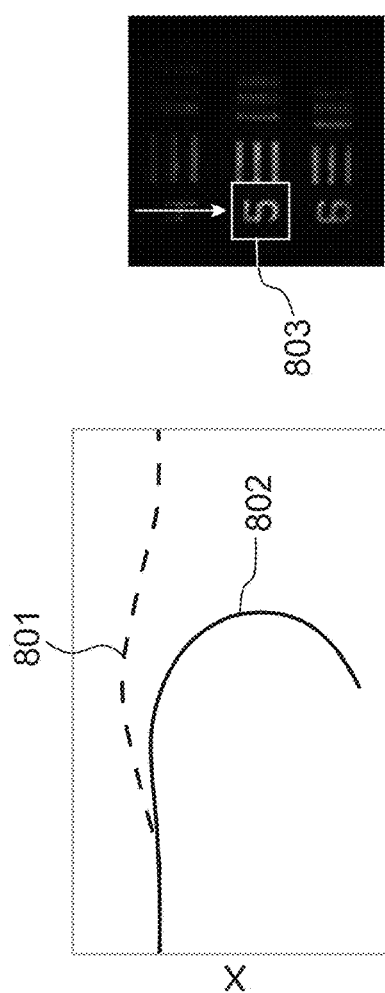
FIG.8A
FIG.8B
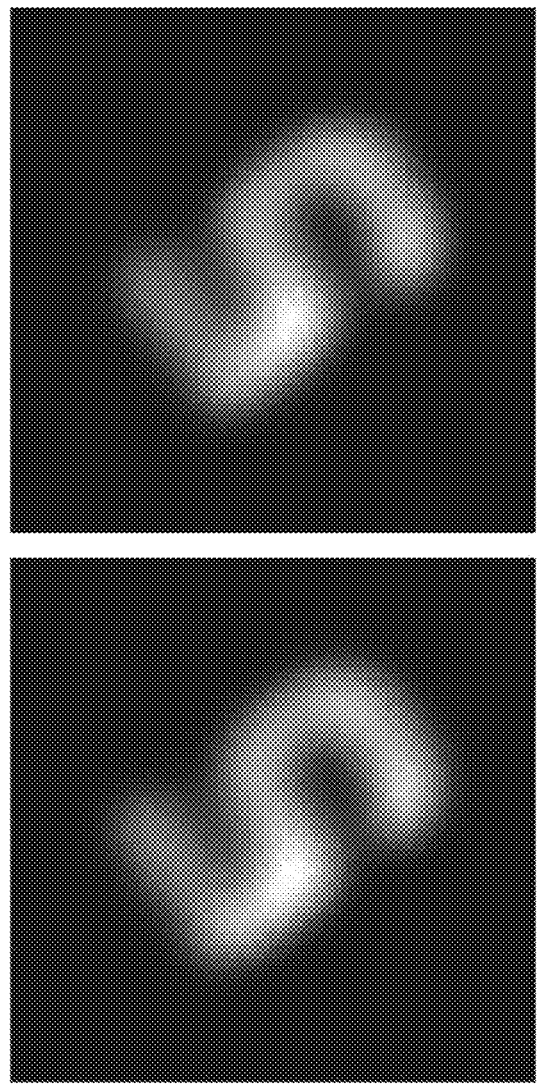
FIG.8C
FIG.8D

DEVICES AND METHODS FOR TRANSPORTING AND CONTROLLING LIGHT BEAMS

PRIOR ART

Technical Field of the Invention

The present invention relates to devices and methods for transporting and controlling light beams, in particular for so-called "lensless" endomicroscopic imaging. It applies for example to endoscopic exploration of organs in a living being, whether human or animal.

Prior Art

The technique of endomicroscopic imaging requires fiber-based optomechanical devices to be used that have specificities with respect to free-space imaging systems.

Specifically, it is not possible to envision the construction of a miniature microscope comprising a light source, a focusing optic and a camera at the distal end (i.e. located at the end of the fiber, on the side of the sample) of a medical endoscope because of the bulk of all these components. Thus, solutions are being sought that will allow imaging to be achieved via the end of an optical fiber while limiting bulk at the distal end of the endoscope.

A technology qualified "lensless endoscopy", and for example described in Cizmar et al. "Exploiting multimode waveguides for pure fiber-based imaging", Nat. Common. 3, 1027 (2012), is in particular known. This technique is based on use of a multimode optical fiber (MMF). The MMF optical fiber is illuminated with a coherent source. On the proximal side (i.e. on the side of the entrance of the optical fiber, on the side opposite the sample) of the MMF, a spatial light modulator (SLM) allows the propagation modes of the fiber to be controlled such that the coherent addition of these modes allows the desired intensity pattern to be generated at the distal end of the MMF. In one embodiment, it is for example sought to produce a focal point at the distal end of the MMF and to scan the sample to obtain an image as would be done in a conventional confocal-microscopy setup.

This technique, which is extremely powerful because of the deterministic character of the transmission matrix of the fiber, which relates a field input into the proximal portion of the fiber to a field output from the distal portion (and vice versa), allows the distal side of the multimode fiber to be freed of optics and thus bulk decreased.

However, the transmission matrix of the fiber is highly dependent on the curvature of the MMF optical fiber. Endomicroscopic imaging by means of an MMF is therefore extremely sensitive to any movement of the fiber. Moreover, due to the multimode character of the fiber, a short pulse in the proximal portion will have elongated by the time it reaches the distal portion, this limiting the possibilities of application to nonlinear imaging, which requires light pulses of high peak intensities to be employed.

In parallel with technologies based on the use of multimode fibers, another "lensless" technology, based on the use of a bundle of single-mode optical fibers (see for example French et al. U.S. Pat. No. 8,585,587), has been developed. In the described technique, a spatial light modulator (SLM) arranged on the proximal side of the bundle of single-mode optical fibers allows, at the distal end of the bundle of fibers, the wavefront emitted by a light source to be controlled. The single-mode character of the fibers eliminates any intermodal dispersion; thus, the only contribution to the dispersion is chromatic dispersion, which is the same for all the single-mode optical fibers and which may therefore be compensated for globally. Therefore, the use of a bundle of single-mode optical fibers is preferred with respect to multimode fibers for the propagation of short pulses.

Various publications have described lensless-endomicroscopy variants based on the use of a bundle of single-mode optical fibers and, more precisely of a multicore fiber (MCF). Thus, for example, it has been shown how, in the distal part of the bundle of optical fibers, a very rapid scan of the focal point may be achieved by varying, by means of a galvanometric device, the angle of the wavefront input into the SLM (see for example E. R. Andresen et al. "Toward endoscopes with no distal optics: video-rate scanning microscopy through a fiber bundle", Opt. Lett. Vol. 38, No. 5, 609-611 (2013)). In E. R. Andresen et al. ("Two-photon lensless endoscope", Opt. Express 21, N° 18, 20713-20721 (2013)), the authors demonstrated the experimental feasibility of a two-photon nonlinear imaging system (TPEF) in lensless endomicroscopy. In E. R. Andresen et al. ("Measurement and compensation of residual group delay in a multi-core fiber for lensless endoscopy", JOSA B, Vol. 32, No. 6, 1221-1228 (2015)), a device for controlling group velocity delays (or "GDC" for "Group Delay Control") with a view to transporting and controlling light pulses in a lensless endomicroscopic imaging system based on the use of a bundle of single-mode optical fibers is described.

FIG. 1A schematically illustrates a lensless endomicroscopic imaging system 100 using a bundle of single-mode optical fibers. The imaging system 100 generally comprises an emission source 10 for emitting an incident light beam Bo, which may be continuous-wave or formed of pulses in the case of application to non-linear imaging. The system 100 moreover comprises a detection channel comprising an objective 21 and a detector 20. The detection channel is separated from the emission channel by a plate beam splitter 22. The imaging system 100 also comprises a device for transporting and controlling the light beams, allowing a remote object 101 of analysis to be illuminated. The transporting and controlling device comprises a bundle 40 of single-mode optical fibers with an entrance face (or proximal face) 41 and an exit face (or distal face) 42, which have been shown enlarged in FIG. 1A, and a spatial light modulator (SLM) 30 that is arranged at the proximal end of the bundle 40 of fibers and that allows the wavefront of the beam emitted by the source 10 to be controlled. The spatial light modulator allows, for each elementary beam $B_i$ intended to enter into an optical fiber $F_i$ of the bundle 40 of fibers, the input wavefront, which has a phase function $\Phi_0$, to be given a given phase shift $\Phi_1(i)$. The phase function $\Phi_1(i)$ will possibly be such that, for example, after propagation through the bundle of optical fibers, the wave has a parabolic phase $\Phi_2(i)$ in the far field. This parabolic phase allows the beam to be focused, on the distal side, on the analysis object 101 even though there is no physical lens present; this is the origin of the terminology "lensless endoscope". More generally, a phase function $\Phi_1(i)$ suitable for generating, as output from the bundle of optical fibers, a given intensity pattern will possibly be induced. Moreover, it is possible, by virtue of the spatial light modulator, to compensate for the intrinsic phase shifts introduced by each of the optical fibers $F_i$.

The bundle of N single-mode optical fibers may be formed from a set of individual single-mode optical fibers, each comprising a core and a cladding, and typically from one hundred to a few tens of thousand fibers that are gathered together to form a bundle of fibers; the bundle of N single-mode optical fibers may also, as illustrated in FIG. 1B, be formed from a set of single-mode cores of a multicore fiber, preferably one with at least a hundred single-mode cores. Thus, in the example of FIG. 1B, a multicore fiber 40 has been shown that comprises a set of single-mode cores $F_i$, an external cladding 43, and also, in this example, an internal multimode cladding 44 suitable for collecting the light signal backscattered, by the object of analysis, from the distal end to the proximal end.

One advantage of the "lensless" technique thus described is in particular that it has a lower sensitivity to movements of the fiber than other techniques, and in particular the MMFs described above. Specifically, the modes of single-mode optical fibers are localized and confined in defined regions in the transverse area of the bundle of optical fibers.

However, as illustrated in FIG. 1C, subjecting the bundle of optical fibers to a curvature results in a translation of the intensity pattern output from the bundle of fibers. Specifically, the curvature of the bundle of fibers causes, for cores located outside the curvature, elongation of the optical path and, in contrast, for cores located inside the curvature, shortening of the optical path. This results in the introduction of an additional phase shift between the cores of the bundle of single-mode fibers. This additional phase shift, which is dependent on the distance of a core (i) from the central core, causes a movement, at the exit of the bundle of fibers, of the point spread function (PSF) of the imaging system, the PSF being the spatial impulse response of the imaging system defined by the SLM and the bundle of single-mode optical fibers. Thus, for example, as illustrated in FIG. 1C, the intensity pattern or PSF, which is represented in this example by a focal point $P_1$ and a number of replicas $R_1$, is translated with respect to the object 101 of observation between situation (1) in which the bundle of fibers is not subjected to curvature and situation (2) in which the bundle of fibers is subjected to a curvature. This movement of the PSF is disadvantageous because, during an observation in vivo, of an organ for example, in the event of a modification of the curvature of the bundle of single-mode optical fibers a change of the observed region of the object will result.

The present invention provides devices and methods for transporting and controlling light beams, in particular for so-called "lensless" endomicroscopic imaging systems, that make the PSF spatially invariant in the event of bending of the bundle of optical fibers, i.e. that allow the intensity pattern to be held still in the frame of reference of the distal end of the bundle of fibers.

SUMMARY OF THE INVENTION

According to a first aspect, the present description relates to a device for transporting and controlling light beams, comprising:
a light guide comprising a bundle of uncoupled single-mode optical fibers, each single-mode optical fiber being intended to receive an elementary light beam at a proximal end and to emit a light beam at a distal end, said bundle of single-mode optical fibers comprising, in operation, a minimum radius of curvature corresponding to a maximum curvature of the bundle of fibers;
an optical device for phase controlling, said device being arranged on the side of the proximal end of the light guide and comprising:
at least a first spatial light modulator suitable for applying a phase shift to each of the elementary beams;
a control unit for controlling the first spatial light modulator, said control unit being configured to apply a phase shift to each of the elementary beams so as to form, at the distal end of the light guide, an illumination beam with a predefined phase function, and wherein said bundle of single-mode optical fibers is twisted, and comprises a twist period defined to preserve said phase function at the distal end of the light guide when the bundle of single-mode optical fibers is subjected to a curvature lower than said maximum curvature.

The phase function is defined such that the PSF, which is also referred to as an intensity pattern in the present description, comprises, for example, one or more focal points, or a predefined intensity pattern depending on the shape of the object to be imaged, or a speckle pattern, i.e. a phase function that on output is random.

By "conservation of the phase function", what is meant is the maintenance of the phase shift between the single-mode optical fibers to lower than $2\pi$ when the twisted bundle of optical fibers is subjected to a curvature lower than said maximum curvature.

The maintenance of the phase shift may be measured by injecting light into two single-mode optical fibers of the bundle of fibers; the intensity pattern at the end of the bundle of fibers then consists of fringes; when the bundle of fibers is subjected to a curvature, a phase shift of lower than $2\pi$ corresponds to a maintenance of the intensity pattern to within one fringe.

The applicants have shown that, in a device for transporting and controlling light beams thus defined, the intensity function at the distal end of the light guide is disturbed very little, in operation, by the curvatures to which the bundle of optical fibers is subjected. As a result, dynamic imaging, whereby it is possible to continuously image an object even when the bundle of fibers is bent, becomes possible.

In the context of the present description, uncoupled single-mode fibers are fibers having the coupling of which is lower than $-20$ dB/m, and advantageously lower than $-30$ dB/m. Uncoupled fibers allow optical beams to be transported and controlled over a bundle of fibers of large length, while allowing inter-core phase shifts to be compensated for.

According to one or more exemplary embodiments, the maximum curvature will possibly not exceed the curvature that a single-mode optical fiber may be subjected to while keeping optical losses below a given threshold value, for example 1 dB/m (corresponding to a transmission of 80% of the energy to the end of 1 m of fibers), and advantageously below 0.5 dB/m. Typically, this corresponds to a minimum radius of curvature higher than or equal to about 2.5 mm.

In practice, however, a maximum curvature of the bundle of single-mode optical fibers will possibly be defined depending on the application. Specifically, depending on the application, endomicroscopy for example, the curvature of the bundle of single-mode optical fibers will depend on the objects to be imaged.

Thus, according to one or more exemplary embodiments, the maximum curvature, in operation, of a bundle of single-mode optical fibers will thus possibly correspond to a minimum radius of curvature higher than or equal to 5 cm, or higher than or equal to 10 cm, or higher than or equal to 20 cm.

According to one or more exemplary embodiments, the length of the bundle of single-mode optical fibers is equal to k times the twist period, where k is an integer. The applicants have shown that this configuration is optimal with regard to obtaining the best conservation of the phase function at the distal end of the bundle of fibers, whatever the maximum curvature of the bundle of single-mode optical fibers.

However, if this condition is not met, the applicants have shown that, for a given half-diameter of the bundle of single-mode optical fibers (distance from the central core to the most distant peripheral core), a range of periods of twist may be defined, depending on the maximum curvature to which the bundle of optical fibers will be subjected in operation, in order to preserve the phase function at the distal end of the light guide.

According to one or more exemplary embodiments, the half-diameter of the bundle of single-mode optical fibers is comprised between 100 and 500 μm, advantageously between 100 and 300 μm, and advantageously between 100 and 200 μm. According to one or more exemplary embodiments, the twist period is longer than 1 mm and advantageously longer than 2.5 mm, to limit the optical losses resulting from the twist.

In practice, for applications in endomicroscopy for example, a twist period comprised between 1 mm and 30 mm and advantageously between 2.5 mm and 10 mm will possibly be chosen.

According to one or more exemplary embodiments, the control unit for controlling the first spatial light modulator is furthermore configured to apply an angular deviation to each of the elementary beams at the proximal entrance of said twisted bundle of single-mode optical fibers, said angular deviation being defined, depending on the position of the single-mode fiber intended to receive said elementary beam in said bundle of single-mode optical fibers, so as to ensure optimal coupling to (or injection of light into) said single-mode fiber. The applicants have shown that this angular correction on the proximal side of the bundle of single-mode optical fibers allows a very good light transmission to be preserved, including in the peripheral single-mode fibers furthest from the central fiber.

According to one or more exemplary embodiments, the light guide comprises at the distal end and/or at the proximal end of said twisted bundle of single-mode optical fibers a section of variable twist period, wherein the twist period tends to infinity on the side of said distal and/or proximal end. In other words, at the interface of the section with free space, all the single-mode optical fibers are parallel. This configuration also allows coupling to the twisted bundle of fibers to be optimized. No angular correction is then required proximal-side.

According to one or more exemplary embodiments, the one or more sections of variable twist period have a length smaller than 5 cm.

According to one or more exemplary embodiments, said variable-twist section has, at said distal and/or proximal end, an untwisted section having a length smaller than 1 cm.

According to one or more exemplary embodiments, the device according to the first aspect is suitable for transporting and controlling light beams comprising optical pulses, for example pulses of pulse durations comprised between 100 fs and 10 ns. Said device may then further comprise a device for controlling the group velocity delays of the light pulses, the latter device being configured to suppress static group velocity delays between the single-mode fibers of said twisted bundle of single-mode optical fibers.

According to one or more exemplary embodiments, at least some of said single-mode optical fibers are doped.

According to one or more exemplary embodiments, the light guide comprises a bundle of N single-mode optical fibers, which is formed from a set of N individual single-mode optical fibers, each comprising a core and a cladding, and typically from one hundred to a few tens of thousands fibers that are gathered together to form a bundle of fibers.

According to one or more exemplary embodiments, the light guide comprises a bundle of N single-mode optical fibers formed from a set of, preferably at least one hundred, single-mode cores. For example, the light guide is a multi-core fiber and the bundle of N single-mode optical fibers is formed by the single-mode cores of the multi-core fiber.

According to one or more exemplary embodiments, the light guide comprises a double-clad multicore fiber; such a multicore fiber has the advantage of being able to transport, with high efficacy, the backscattered light signal in one cladding of the double-clad multicore fiber, which is generally a multimode cladding.

By "single-mode optical fiber", what is meant is a fiber through which light is able to propagate only in a single mode of the electromagnetic field; by extension, what is also meant is a so-called "effective single-mode" fiber the conditions of coupling to which are such that, even though it is able to maintain a plurality of modes, only a single mode (generally the fundamental mode) is excited, to which mode the light is confined throughout propagation (no coupling or very weak coupling with the other modes).

Throughout this description, the term "single-mode core" or "a single-mode optical fiber" will be used to refer either to an individual single-mode optical fiber or to a single-mode core of a multicore fiber.

According to one or more exemplary embodiments, the first spatial light modulator comprises a segmented or membrane deformable mirror, for operation in reflection.

According to one or more exemplary embodiments, the first spatial light modulator comprises a matrix-array of liquid crystals, for operation in reflection or in transmission.

According to one or more exemplary embodiments, the control unit for controlling the first spatial light modulator is configured to apply a phase shift to each of the elementary beams so as to form, at the distal end of the light guide, an illumination beam with a phase function that varies as a function of time. For example, it will thus be possible to scan the region to be illuminated.

According to one or more exemplary embodiments, the single-mode fibers are arranged periodically or quasi-periodically within the bundle of fibers.

According to one or more exemplary embodiments, the single-mode fibers are arranged aperiodically within the bundle of fibers, this allowing the intensity of "replicas" in the image plane, i.e. of focal points of lower intensity that encircle a brighter central focal point, to be notably decreased.

According to a second aspect, the present description relates to an endomicroscopic imaging system comprising a light source; a device according to the first aspect for transporting and controlling the light beams emitted by said source in order to form an illumination beam for illuminating an object with a defined phase function; and a detection channel for detecting the light returned by the object and transmitted through said at least one light guide, from its distal end to its proximal end.

According to a third aspect, the present description relates to a method for transporting and controlling light beams, comprising:

receiving elementary light beams at a proximal end of a bundle of N single-mode optical fibers of a light guide, wherein:
each single-mode optical fiber is intended to receive an elementary light beam and to emit a light beam at a distal end;

said bundle of single-mode optical fibers comprises, in operation, a minimum radius of curvature corresponding to a maximum curvature of the bundle of fibers; and said bundle of single-mode optical fibers is twisted, and comprises a twist period;

applying, by means of at least a first spatial light modulator arranged on the side of the proximal end of said bundle of single-mode optical fibers, a phase shift to each of the elementary beams, in order to form, at the distal end of the light guide, an illumination beam with a defined phase function, said twist period being defined to preserve said phase function at the distal end of the light guide when the bundle of single-mode optical fibers is subjected to a curvature lower than said maximum curvature.

According to one or more exemplary embodiments, the application of the phase shift to each of the elementary beams aims to achieve, at the distal end of the section of multimode optical fiber, a phase function defined so as to form an illumination beam that converges at a given distance from an exit face of the section of multimode optical fiber, allowing one or more focal points to be formed.

According to one or more exemplary embodiments, the application of successive phase shifts to each of the elementary beams allows the focal point to be scanned in a plane at said given distance from the exit face of the section of multimode optical fiber and/or to various distances from the exit face of the section of multimode optical fiber.

According to one or more exemplary embodiments, the application of the phase shift to each of the elementary beams aims to achieve, at the distal end of the section of multimode optical fiber, a phase function defined so as to form predefined intensity pattern depending on the shape of the object to be imaged, or a speckle pattern.

According to one or more exemplary embodiments, the method furthermore comprises applying an angular deviation to each of the elementary light beams at the proximal entrance of said twisted bundle of single-mode optical fibers, said angular deviation being defined, depending on the position of the single-mode fiber intended to receive said elementary beam in said bundle of single-mode optical fibers, to optimize the coupling to said single-mode fiber.

According to one or more exemplary embodiments, the method is suitable for transporting and controlling light beams comprising optical pulses, and furthermore comprises suppressing static group velocity delays between the single-mode fibers of said twisted bundle of single-mode optical fibers by means of a device for controlling the group velocity delays of the light pulses.

According to one or more exemplary embodiments, the method furthermore comprises a prior calibration that allows the phase shift to be applied to each of the elementary beams depending on the phase function sought for the illumination beam to be determined.

According to one or more exemplary embodiments, the prior calibrating step comprises partially or fully determining a transmission matrix of the bundle of single-mode optical fibers.

According to a fourth aspect, the present description relates to an endomicroscopic imaging method employing no lens distal side, comprising:

emitting light beams;

transporting and controlling the light beams by means of a method according to the third aspect so as to illuminate an object with said illumination beam;

detecting the light returned by the object and transmitted through the light guide, from its distal end to its proximal end.

The light returned by the object may be of different nature depending on the application; for example the returned light is backscattered light, or the emitted light, for example light emitted via a fluorescence mechanism.

BRIEF DESCRIPTION OF THE DRAWINGS

Other advantages and features of the invention will become apparent on reading the description, which is illustrated by the following figures:

FIGS. 8C and 8D, comparative images of a test pattern (FIG. 8B) obtained with an unbent and bent bundle of fibers (FIG. 8A);

DETAILED DESCRIPTION

In the detailed description which follows, only some embodiments are described in detail in order to ensure clarity of the description, but these examples are not intended to limit the general scope of the principles that emerge from the present description.

The various embodiments and aspects described in the present description may be combined or simplified in multiple ways. In particular, the steps of the various methods may be repeated, reversed, or performed in parallel, unless otherwise specified.

When, in the present description, reference is made to computing or processing steps for, in particular, implementing steps of methods, it will be understood that each computing or processing step may be implemented by software, hardware, firmware, microcode or any suitable combination of these technologies. When software is used, each computing or processing step may be implemented via computer-program instructions or software code. These instructions may be stored on or transmitted to a storage medium that is readable by a computer (or control unit) and/or be executed by a computer (or control unit) in order to implement these computing or processing steps.

Figure 2:
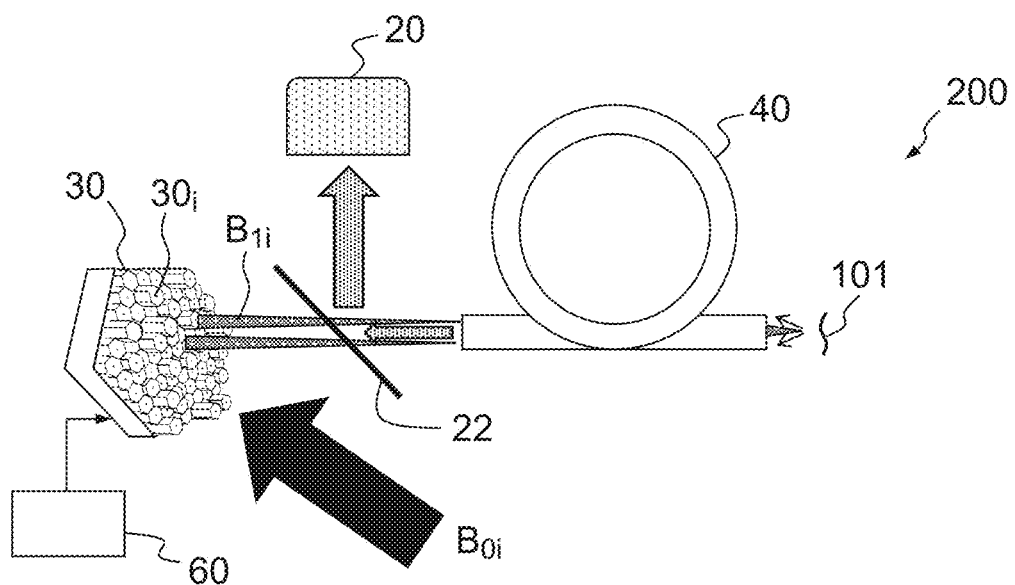
FIG. 2, a schematic diagram illustrating an example of a lensless endomicroscopic imaging system according to the present description.

FIG. 2 schematically illustrates an example of a "lensless" endomicroscopic imaging system 200 with a device for transporting and controlling light beams according to the present description, which is suitable for imaging an object referenced 101 in FIG. 2.

The endomicroscopic imaging system 200 comprises a light source (not shown in FIG. 2) suitable for the emitting light beams $B_{0i}$, the light beams possibly comprising light pulses in the case of an application to nonlinear imaging. Thus, the light source for example comprises a laser source and, if necessary, an optical system for enlarging and collimating the emitted light beams.

The endomicroscopic imaging system 200 moreover comprises a device for transporting and controlling the light beams emitted by said light source in order to illuminate the object 101 with a chosen intensity pattern, for example one taking the form of one or more focal points, which are for example scanned over the field, or, depending on the application, taking another form. The device for transporting and controlling the light beams generally comprises a light guide 40 comprising a twisted bundle of single-mode optical fibers (or "MCF"), as will be explained in more detail below, and an optical phase-controlling device arranged on the side of a proximal end of the first light guide, and in particular comprising a spatial light modulator 30.

The twisted bundle of single-mode optical fibers may comprise a set of individual single-mode optical fibers, typically from one hundred to a few tens of thousand fibers that are gathered together to form a bundle of fibers, or may comprise a set of, preferably at least a hundred, single-mode cores of a multicore fiber. The multicore fiber is for example a double-clad fiber.

The light guide 40 may comprise other elements, for example any element useful for producing the guide, such as protective elements, as known to those skilled in the art. In the case of a double-clad multicore fiber, one cladding may be a multimode cladding, suitable for the propagation of the light flux backscattered by the object.

Advantageously, the coupling between the single-mode cores of the bundle of single-mode optical fibers is lower than −20 dB/m and advantageously lower than −30 dB/m, this allowing the optical beams to be transported and controlled over a bundle of fibers of large length, while allowing the effects of inter-core phase shift to be compensated for.

The length of the single-mode fibers of the bundle of fibers is tailored to the application, to the length required for an endoscopic microscope for example. Typically, the length of the single-mode fibers of the bundle of fibers is comprised between 30 cm and 3 m.

The optical device for phase controlling is arranged on the side of the proximal end of the bundle of single-mode optical fibers and comprises the spatial light modulator 30, which is suitable for applying a phase shift to each of the elementary beams $B_{0i}$, and a control unit 60 for controlling the first spatial light modulator, which allows a phase shift to be applied to each of the elementary beams so as to achieve, at the distal end of the light guide 40, a predefined phase function. The spatial light modulator 30 may for example comprise a segmented or membrane deformable mirror, for operation in reflection, or a matrix-array of liquid crystals, for operation in reflection or transmission. In the example of FIG. 2, each elementary surface $30_i$ of the spatial light modulator 30 allows a given phase shift $\Phi_1(i)$ to be applied to one elementary light beam $B_{0i}$, so as to form an elementary beam $B_{ji}$, intended to enter into one optical fiber $F_i$ of the light guide 40.

For example, as illustrated in FIG. 2, the phase function $\Phi_1(i)$ is defined to form, at the distal end of the light guide 40, in the far field, a beam that converges to form a focal point in a plane that is located at a given distance from the exit face of the light guide 40 and that comprises the object of interest 101.

The device for transporting and controlling light beams is said to be "lensless" because it does not comprise any lenses on the distal side, i.e. on the side of the emergence of the light beams, the phase being controlled by the phase-controlling device arranged on the side of a proximal end of the device.

Provision may be made for a prior calibration of the device with a view to determining the phase shift to be applied to each of the elementary beams depending on the phase function sought for the illumination beam. This prior calibrating step may comprise determining a transmission matrix of the bundle of single-mode optical fibers. In the case of a bundle of single-mode optical fibers with low inter-core coupling, the transmission matrix may be a diagonal matrix relating the input and output fundamental modes of each core. In this case it will be enough to measure, at a single wavelength (typically the central wavelength of the laser light source used), only the relative phase shifts acquired by the elementary beams after having passed through the bundle of optical fibers.

According to one exemplary embodiment, the imaging system 200 may also comprise means (not shown in FIG. 2) for focusing the elementary light beams $B_{0i}$ on the elements $30_i$ of the spatial light modulator 30. The means for focusing the elementary light beams $B_{0i}$ for example comprise a matrix-array of microlenses or a spatial light modulator, for example a matrix-array of liquid crystals forming a two-dimensional tiling of gratings having quadratic phases, thus simulating a matrix-array of microlenses.

The endomicroscopic imaging system 200 also comprises a detection channel for the light backscattered by the object 101 and transmitted through the light guide 40 from its distal end to its proximal end. In the example of FIG. 2, the detection channel comprises a plate beamsplitter 22, a detector 20 and optionally an objective (not shown in FIG. 2) for focusing the backscattered light onto a detection surface of the detector 20, and a unit (not shown) for processing the signals generated by the detector 20.

Figure 3A:
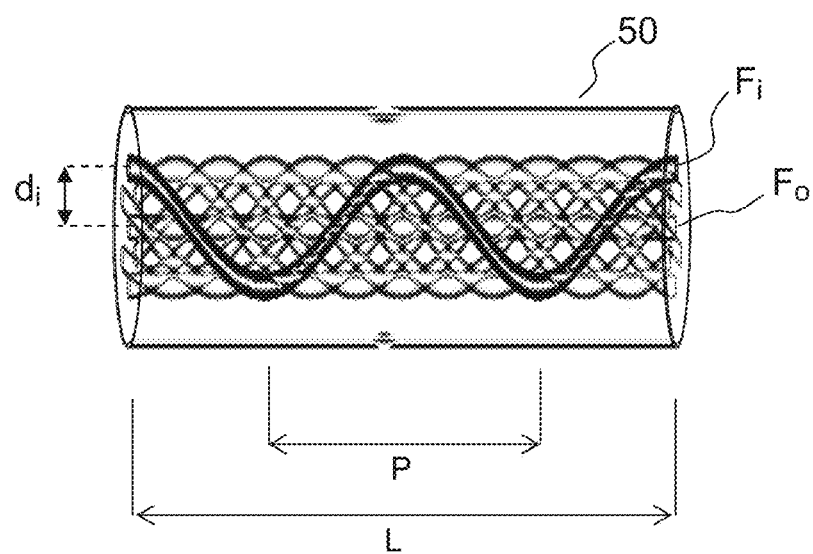
FIGS. 3A to 3C, figures illustrating a twisted bundle of single-mode fibers according to examples of the present description and FIG. 3D, a figure illustrating the preservation of the intensity pattern during bending of a bundle of fibers according to the present description.
Figure 3B:
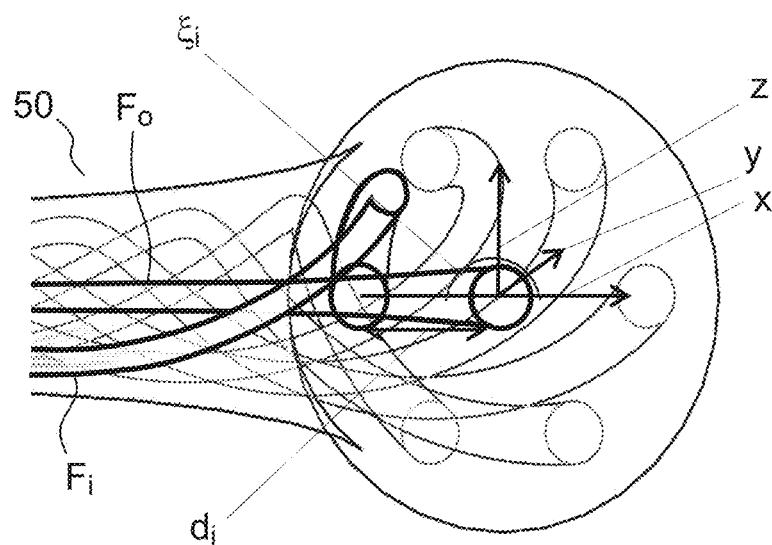
Figure 3C:
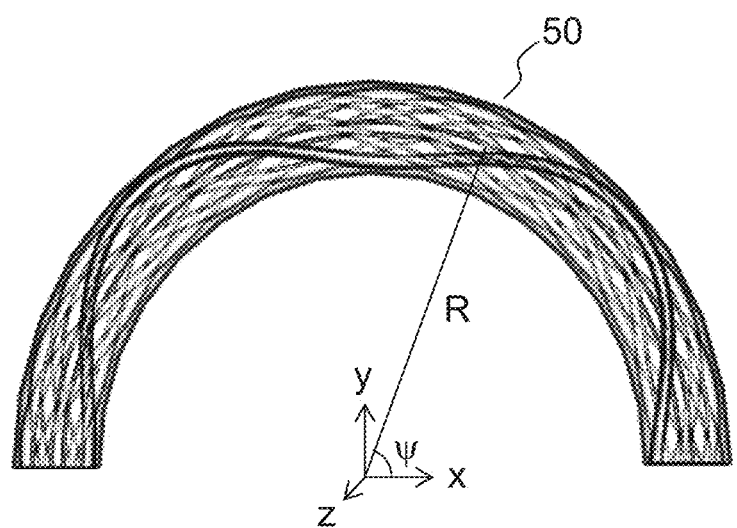

An example of a twisted bundle 50 of single-mode optical fibers according to the present description is illustrated in FIGS. 3A to 3C.

A twisted bundle 50 of single-mode optical fibers (or cores) generally comprises a rectilinear central core $F_0$ and a set of cores Fi wound around the central core $F_0$ helically. The length L of the bundle of single-mode optical fibers corresponds to the length of the central core $F_0$. The twisted bundle 50 of single-mode fibers comprises a twist period P. As illustrated in FIG. 3B, each core Fi may be characterized by a distance $d_i$ with respect to the central core $F_0$ and an angle $\zeta_i$ defined by the azimuthal angle of the core $F_i$ on the entrance face of the MCF (FIG. 3B). For a given core, $d_i$ and $\zeta_i$ are constant. A half-diameter d of the bundle of single-mode optical fibers may be defined as the distance from the central core to the furthest core. Typically, the half-diameter d is comprised between 100 μm and 500 μm, advantageously between 100 μm and 300 μm, and advantageously between 100 μm and 200 μm.

When the bundle of single-mode optical fibers 50 is subjected to a curvature (FIG. 3C), a radius of curvature R of the curvature, which corresponds to the radius of curvature of the central core, at a polar coordinate $\psi$ defined in FIG. 3C with respect to the center of curvature, is defined locally. In the remainder of the description, the minimum radius of curvature of the bundle 50 of single-mode optical fibers corresponds to the maximum local curvature of the bundle 50 of single-mode optical fibers, in operation.

Figure 1A:
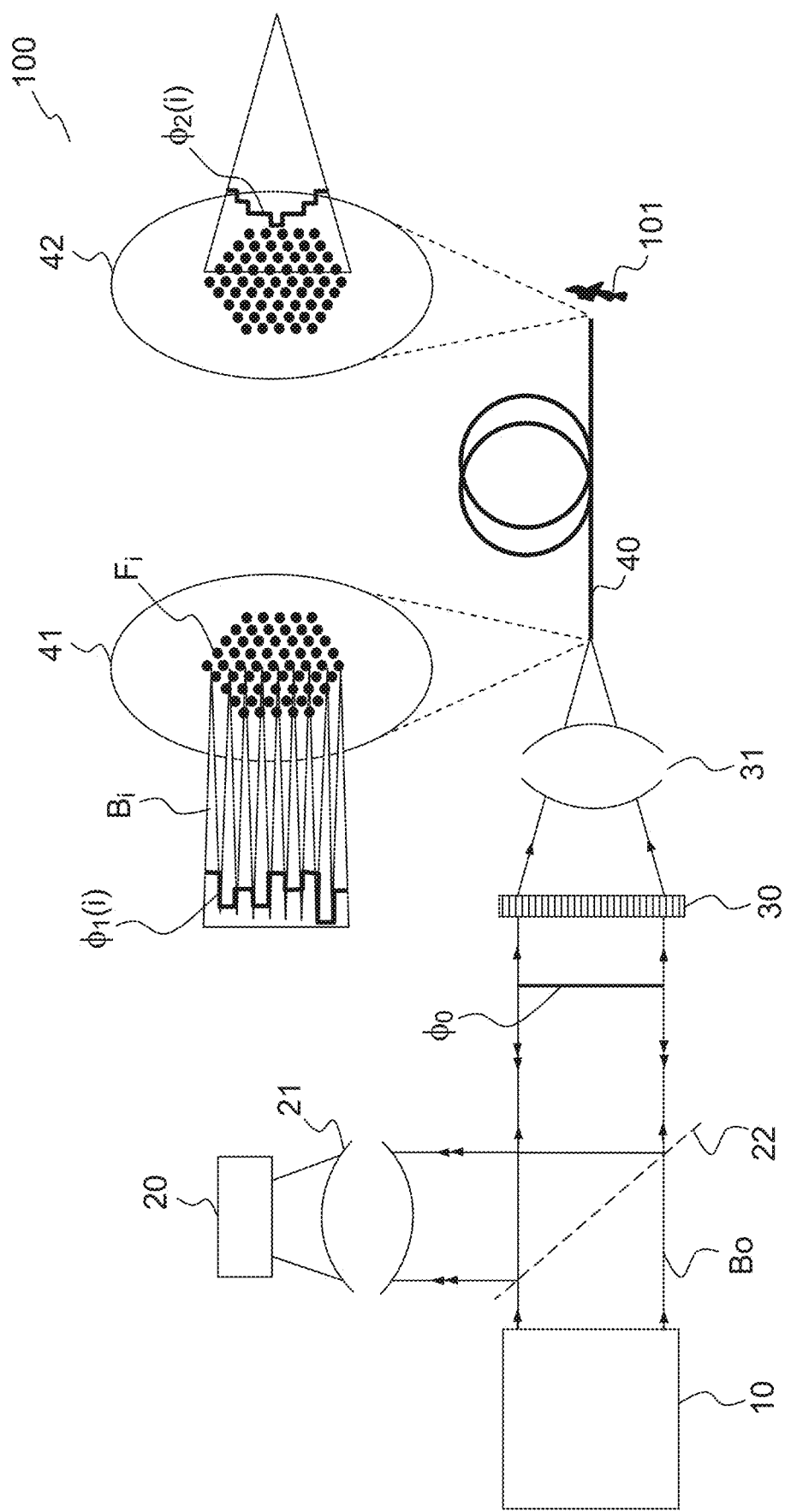
FIGS. 1A to 1C (which have already been described), a schematic diagram of a so-called "lensless" endoscope according to the prior art, based on the use of a bundle of single-mode fibers (FIG. 1A); a set of single-mode cores of a multicore fiber according to the prior art (FIG. 1B); a figure illustrating the movement of the intensity pattern during bending of a bundle of fibers according to the prior art (FIG. 1C)
Figure 1B:
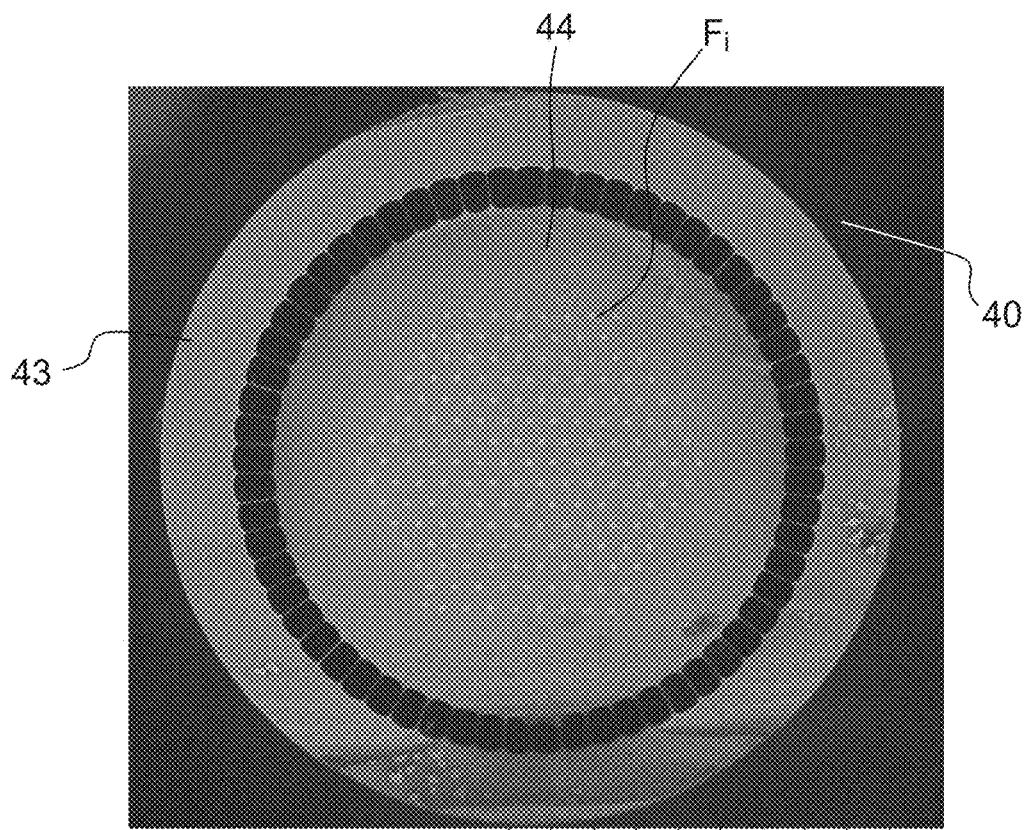
Figure 1C:
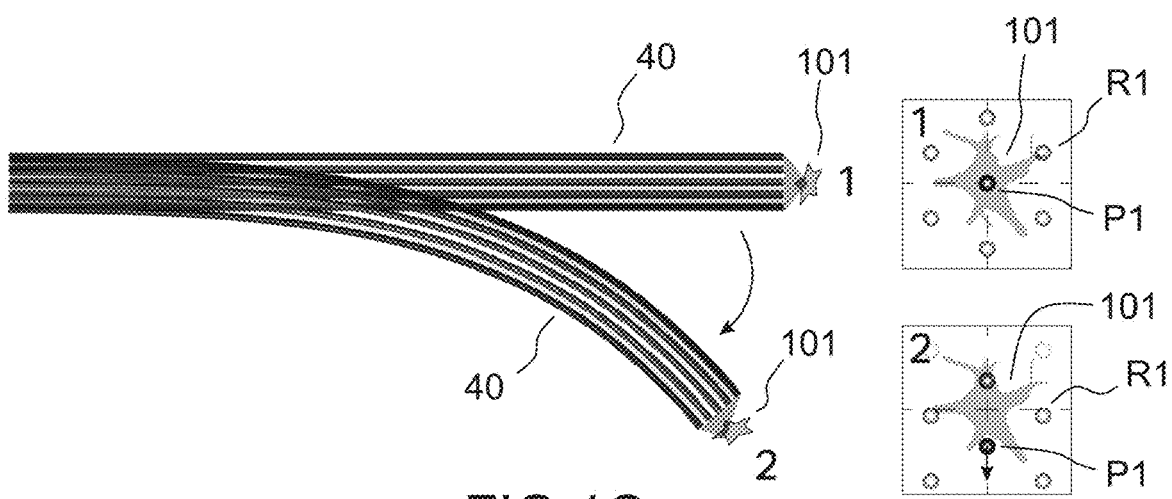
Figure 3D:
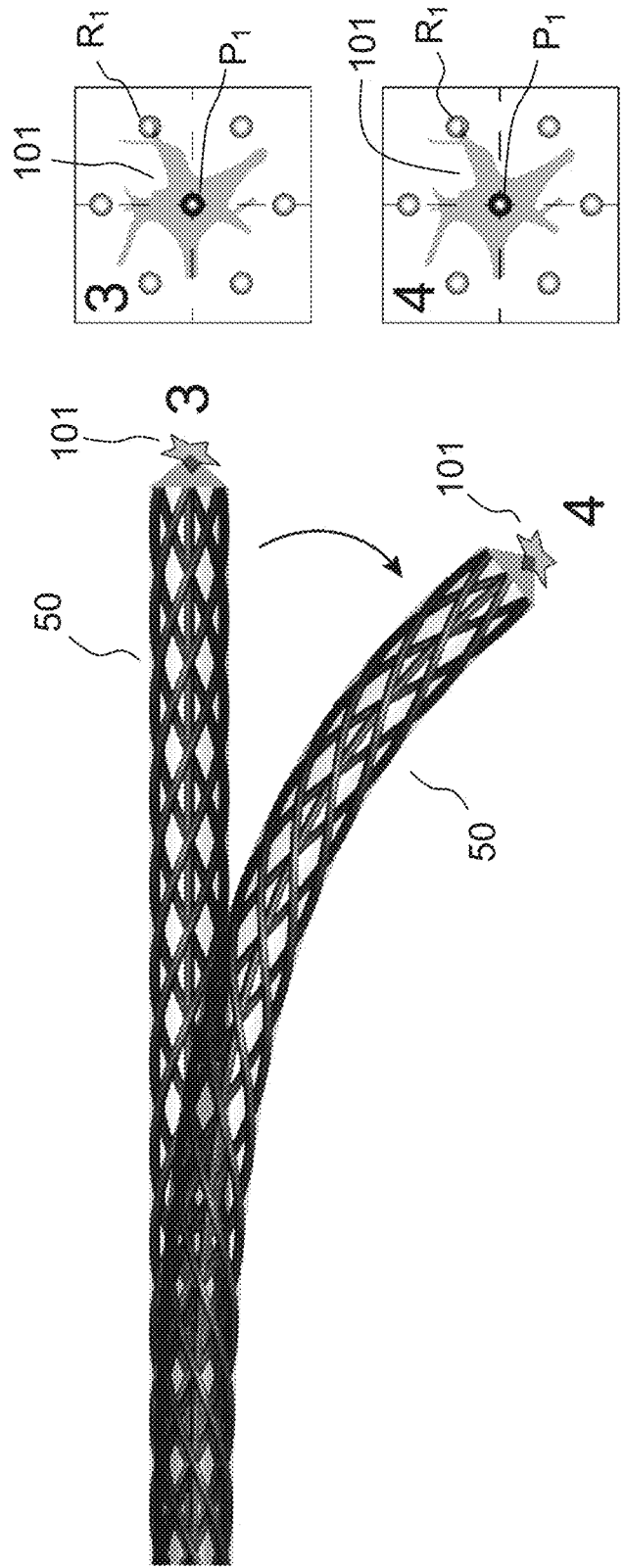

FIG. 3D illustrates the preservation of the intensity pattern during bending of a bundle of fibers according to the prior art. In comparison with an untwisted bundle of fibers according to the prior art (see FIG. 1C), the applicants have shown that an excellent preservation of the phase function may be obtained at the distal end of the bundle of fibers, and thus preservation of the intensity pattern.

The applicants have shown that it is possible to define, depending on the minimum radius of curvature in operation, a twist period P of the bundle of single-mode optical fibers that will allow the intensity pattern at the distal end of the light guide 40 to be preserved.

More precisely, the applicants have shown that, if the length L of the bundle of fibers is such that L/P=k (with k an integer), i.e. if the length of the bundle of fibers is an integer number of times the twist period, then the twisted bundle of fibers is insensitive to bending and the additional phase shift between the cores is zero. It is thus possible for the bundle of optical fibers to be given radii of curvature as small as a few millimeters without modification of the intensity pattern at the distal exit of the bundle of fibers.

In this case, the lower limit $P_{min}$ of the value of the period corresponds to the maximum curvature that a single-mode core may be subjected to without causing optical losses higher than a given threshold value. Thus, for example, for an optical-loss threshold set to 1 dB/m (i.e. 80% of the energy is transmitted to the end of 1 m of fiber), the applicants have shown that the period could advantageously be longer than 2.5 mm.

The applicants have also shown that if L/P is not an integer, i.e. if L/P=k+δL (with k an integer), the additional phase shift $\Delta(\Delta\Phi)$ of those cores of the bundle of fibers that are subjected to a curvature is not zero, but dependent on $d_i$, $\zeta_i$, P, R (minimum radius) and δL.

Figure 4A:
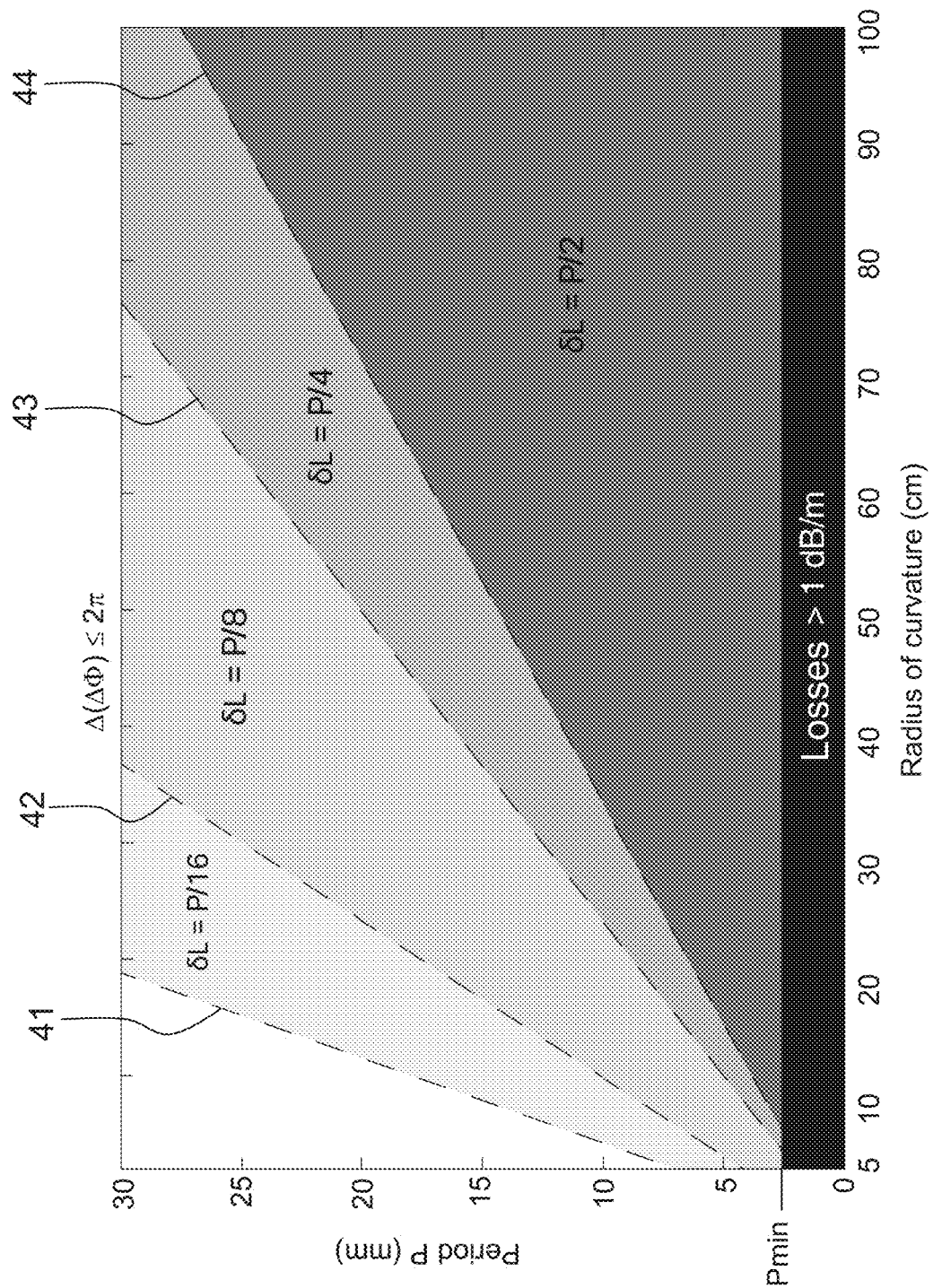
FIG. 4A, a graph illustrating the conditions of preservation of the phase function for given radii of curvature (on the x-axis) and given twist periods (on the y-axis) of the twisted bundle of optical fibers, for a half-diameter of the bundle of fibers of 100 μm and for various fiber lengths kP+δL, where k is an integer, P is the twist period, and δL is P/2, P/4, P/8 and P/16, respectively.

FIG. 4A thus illustrates, for various values of δL, the relationship (represented by a dashed line) that there must be between the twist period P and the minimum radius of curvature if an additional phase shift between the central core and a core located on the periphery of the bundle of fibers of 2π is to be achieved. For each value of δL, the values below the corresponding dashed line correspond to values $\Delta(\Delta\Phi) \leq 2\pi$. Thus, the dashed line 41 corresponds to a value $\Delta(\Delta\Phi)=2\pi$ for δL=±P/16, the dashed line 42 corresponds to a value $\Delta(\Delta\Phi)=2\pi$ for δL=±P/8, the dashed line 43 corresponds to a value $\Delta(\Delta\Phi)=2\pi$ for δL=±P/4, and the dashed line 44 corresponds to a value $\Delta(\Delta\Phi)=2\pi$ for δL=±P/2.

The curves were computed using equations describing the propagation of light in a twisted fiber and given for example in Napiorkowski et al. "*Rigorous simulations of a helical fiber by the use of transformation optics formalism*", Opt. Express 22(19), 2014. More precisely, for the computation of the curves of FIG. 4A, the considered distance d (or half-diameter) between the central core and a core located on the periphery was 100 μm, and the bundle of fibers was considered to have a curvature such as to introduce a maximum phase shift between the central core and the core located on the periphery of the bundle of fibers.

It may be seen from this figure that the smaller δL, the less it will be necessary to "twist" the bundle of optical fibers for a given minimum radius of curvature. In other words, it is possible to choose a twist period that is long enough and not to employ the minimum value $P_{min}$ of the period defined to ensure a defined optical-loss threshold is not exceeded.

For example, in the example illustrated in FIG. 4A, if the worst case scenario (δL=P/2) is considered and if a maximum curvature of the bundle of fibers in operation corresponding to a radius of curvature of 30 cm is assumed, a twist period of about 8 mm will possibly be chosen to preserve the phase function at the distal end of the light guide. It may be seen that it will be difficult, under this assumption, to preserve the phase function without loss of light if the radius of curvature is as small as 10 cm. In contrast, with lower δL values, it will be possible to preserve the phase function without loss of light and it will be possible to choose longer twist periods.

Figure 4B:
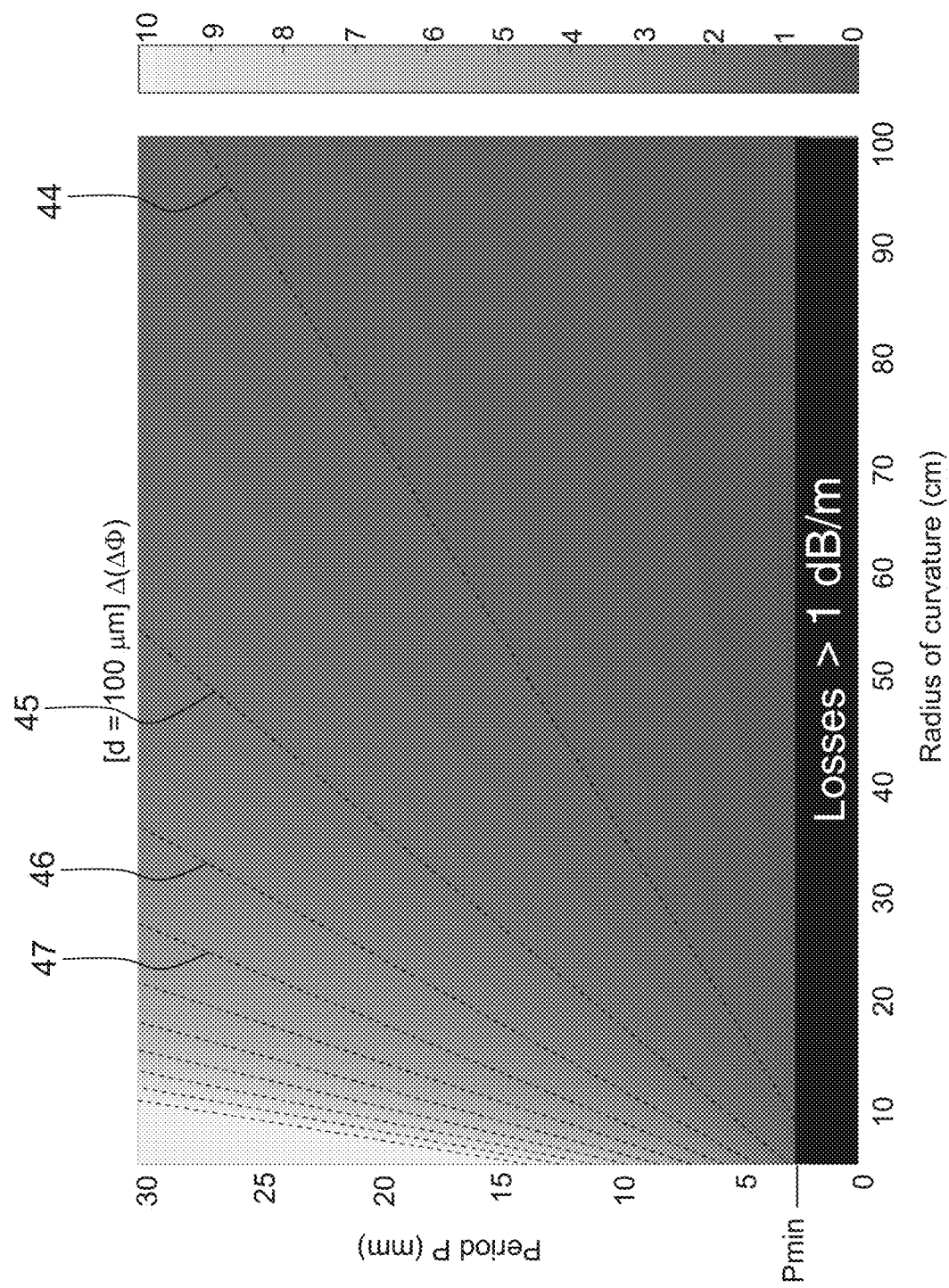
FIGS. 4B and 4C, graphs illustrating the additional phase difference between a single-mode core on the periphery of the bundle of fibers and a central core, for given radii of curvature (x-axis) and given twist periods (y-axis) of the twisted bundle of optical fibers, for a half-diameter of the bundle of fibers of 100 μm (FIG. 4B) and 200 μm (FIG. 4C) and a fiber length kP+P/2, where k is an integer and P is the twist period.
Figure 4C:
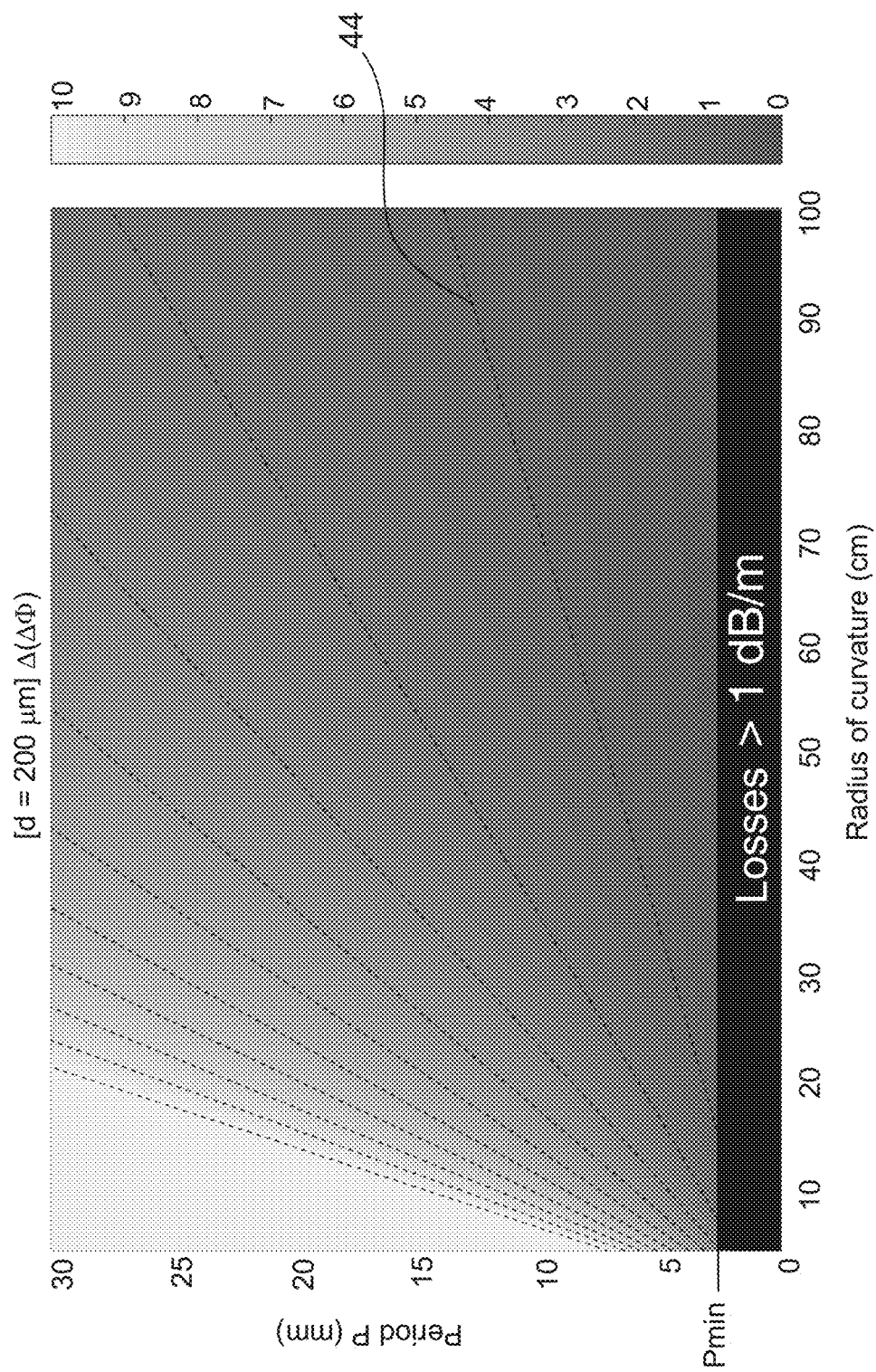

FIGS. 4B and 4C show the additional phase shift $\Delta(\Delta\Phi)$ for a distance d between the central core and a core located on the periphery of 100 μm (diameter of the bundle of fibers 200 μm) and a distance d between the central core and a core located on the periphery of 200 μm (diameter of the bundle of fibers 400 μm), respectively. In these figures, it is assumed that δL=/P2 (worst case scenario). The dotted line 44 corresponds, as above, to a value $\Delta(\Delta\Phi)=2\pi$. and the other lines 45, 46, 47, etc. correspond to additional phase-shift values $\Delta(\Delta\Phi)$ of 4π, 6π, 8π, etc. In practice, a twist-period value will be chosen to preserve an additional phase shift lower than 2π when the bundle of fibers is subjected, in operation, to a maximum curvature corresponding to a given minimum radius of curvature.

It may be seen, by comparing FIGS. 4B and 4C, that for a given radius of curvature, a longer twist period, and therefore one further from the determined minimum period, will possibly be chosen so as not to exceed a defined optical-loss threshold, with bundles of optical fibers of smaller diameters.

In practice, the diameters of the bundles of optical fibers are generally smaller than 400 μm, this demonstrating the feasibility of our method for preserving the phase function at the distal end of the bundle of optical fibers.

A twisted bundle of single-mode optical fibers according to the present description may be manufactured by known means, as described for example in P. S. J. Russell et al. ("*Helically twisted photonic crystal fibers*" Philosophical Transactions of the Royal Society A: Mathematical, Physical and Engineering Sciences 375 (2017)).

According to a first example, the preform is rotated when the bundle of fibers is pulled. This technique uses a rotary motor (which spins at a few thousand revolutions per minute) and a rotary joint. The twist period is thus equal to the drawing speed (in m/s) divided by the rotation frequency (in Hz) of the preform. With this approach, it is possible to obtain twist periods of a few millimeters over lengths of 100 m of fiber.

According to a second example, the rotational twisting is performed after the bundle of fibers has been pulled. To do this, the bundle of fibers is mounted between a rotary motor and a fixed holder, then a CO2 laser is used that, focused on the bundle of fibers, melts the silica. Controlling the focal spot of the CO2 laser, its exposure time, and its movement over the rotating bundle of fibers allows the parameters of the twist to be controlled. This technique allows the twist period to be varied over the length of the bundle of fibers.

The applicants have also shown how it is possible to improve the coupling to the single-mode cores of a twisted bundle of optical fibers.

Figure 5:
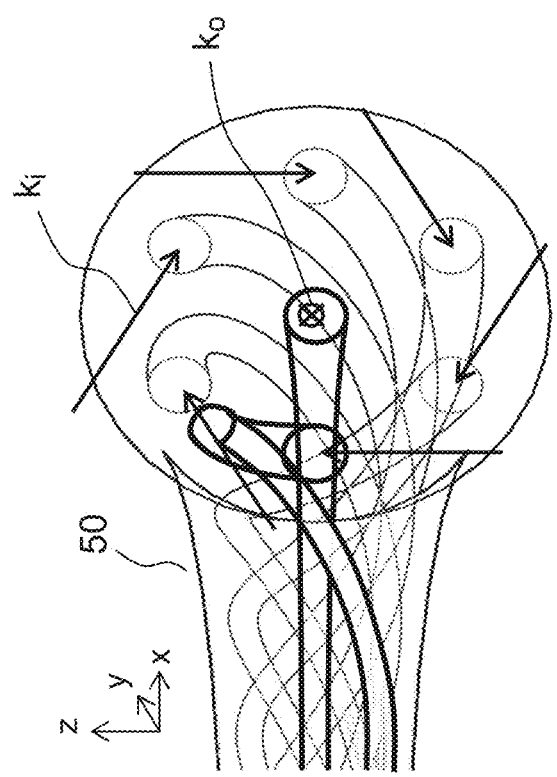
FIG. 5, a schematic illustrating the application of an angular deflection at the entrance of the fiber to optimize coupling.

FIG. 5 shows the entrance face of the twisted MCF 50. The fundamental mode of the central core propagates parallel to the axis of the MCF; in other words its propagation vector $k_{(i=0)}$ (represented by a cross on the central fiber) is parallel to the axis of the MCF. The elementary beam that enters the central core with the highest coupling efficiency is the one the propagation vector of which is equal to $k_0$, i.e. an elementary beam that also propagates parallel to the axis of the MCF. The situation is different for off-center cores: Due to the helicity of these cores, the fundamental mode in these cores propagates at an angle with respect to the axis of the MCF; in other words, the propagation vector $k_i$ for an off-center core is not parallel to the axis of the MCF. To ensure optimal coupling, the applicants have shown that it is advantageous for each elementary beam that enters into an off-center core to have a propagation vector equal to $k_i$ and thus to make an angle to the axis of the MCF.

Figure 6A:
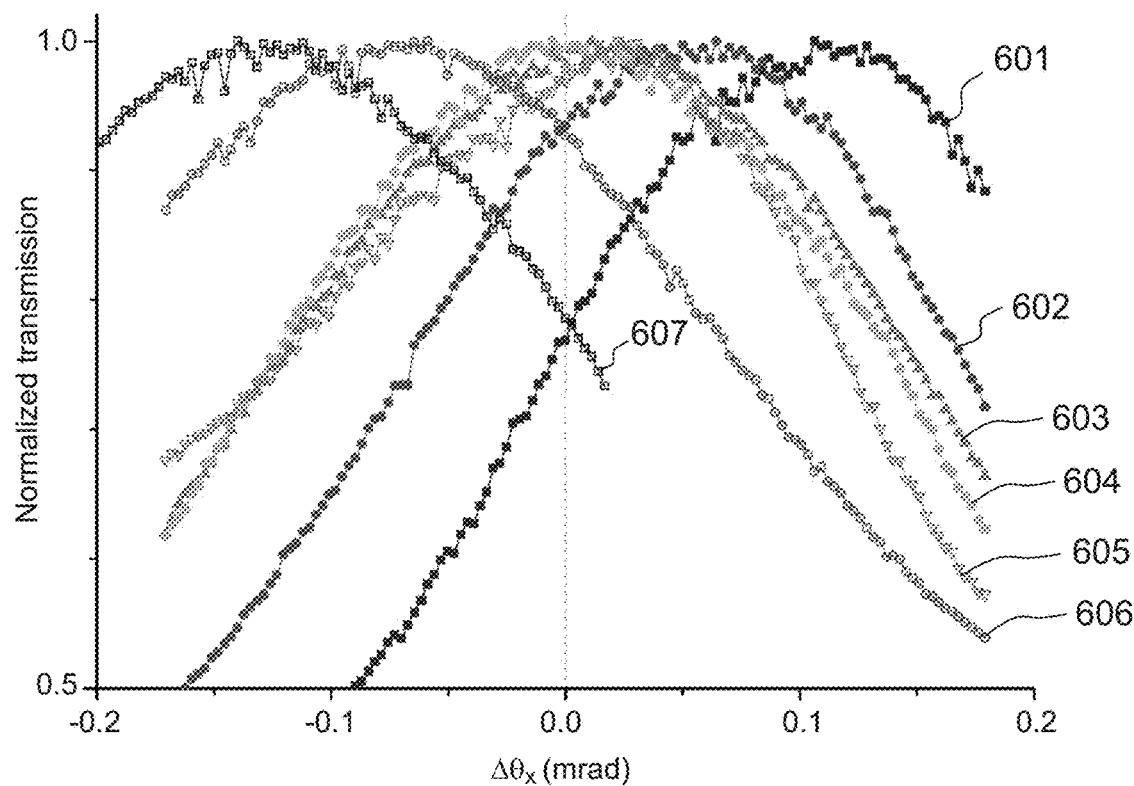
FIGS. 6A and 6B, curves illustrating normalized transmission as a function of application of x-wise angular deviation (FIG. 6A) and y-wise angular deviation (FIG. 6B) depending on the position (illustrated in FIG. 6C) of the core with respect to the central core, and FIG. 6D a curve illustrating the normalized transmission of a core as a function of its distance from the central core without application of an angular deviation and with application of an angular deviation.

More precisely, the applicants have taken measurements showing the influence of the angular deviation $\Delta\theta_x^{(i)}$ (FIG. 6A) and of the angular deviation $\Delta\theta_y^{(i)}$ (FIG. 6B) on the normalized transmission of single-mode cores $F_i$ located at various distances $d_i$ from the central core. FIG. 6C shows the position of the core $F_i$ expressed in number of times the distance $\Lambda$ between two neighboring cores of the MCF (or pitch of the MCF). Thus, position +7 corresponds to a core $F_i$ located at a distance $d_i$ equal to 7Λ from the central core, where Λ is the pitch of the MCF.

Figure 6B:
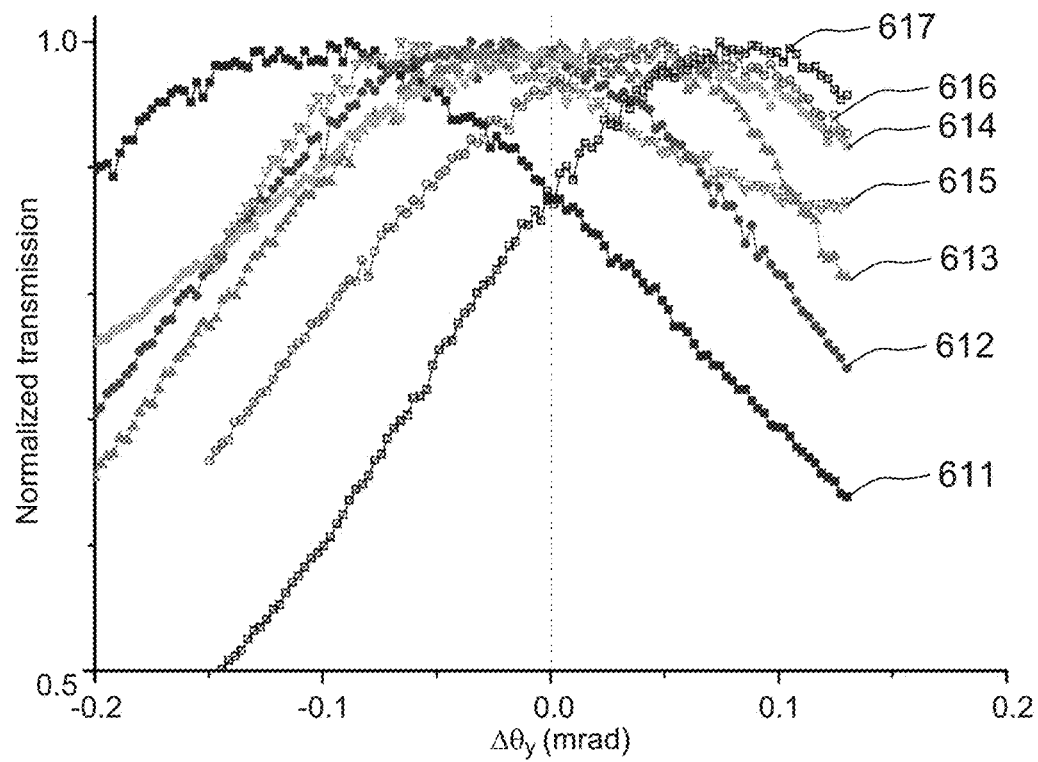
Figure 6C:
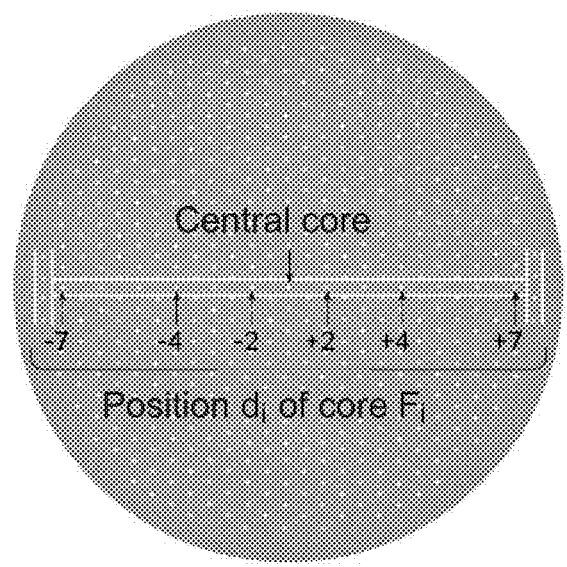

In FIG. 6B, curves 601-607 correspond to cores located at distances from the central core equal to −7Λ, −4Λ, −2Λ, 0, +2Λ, +4Λ, +7Λ., respectively.

In FIG. 6C, curves 611-617 correspond to cores located at distances from the central core equal to −7Λ, −4Λ, −2Λ, 0, +2Λ, +4Λ, +7Λ., respectively.

These curves illustrate that the normalized transmission is maximized by applying an angular deviation $\Delta\theta_x^{(i)}$, $\Delta\theta_y^{(i)}$ that depends on the distance from the core $F_i$ to the central core $F_0$.

Figure 6D:
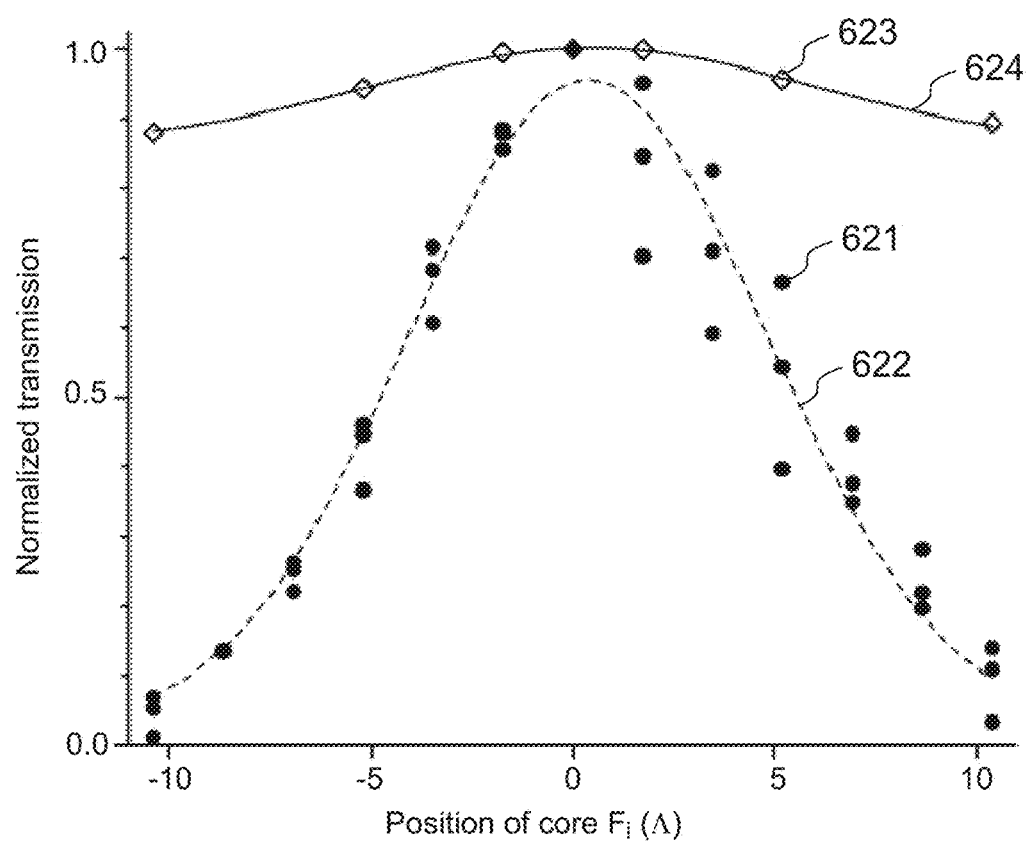

FIG. 6D shows the normalized transmission of a core $F_i$ as a function of its distance from the central core $F_0$ (in number of times the distance Λ between two neighboring cores of the MCF (or pitch)) without application of an angular deviation (curves 621 and 622) and with application of an angular deviation (curves 623 and 624). It may be seen that applying an angular deviation allows the coupling to optical fibers the distance of which with respect to the center is large to be significantly increased. For example, for a core located at 10 Λ from the central core, an angular deviation of 0.15 mrad in x and y allows coupling to be increased by 80% (increase from 10% without angular deviation to 90% with angular deviation).

It will be noted that it is the transverse portion of the propagation vector that is preserved through the interface between free space and the twisted MCF (because the moment is conserved). In terms of propagation angles, the angles are a factor n larger in free space than in the MCF, n being the refractive index of the glass from which the MCF is made.

Thus, it is advantageous to make provision to apply an angular deviation Oi to each of the elementary beams $B_{1i}$ at the proximal entrance of said twisted bundle of single-mode optical fibers (see FIG. 2), said angular deviation Oi being defined, depending on the position of the single-mode core $F_i$ intended to receive the elementary beam in said bundle of single-mode optical fibers, in order to improve the coupling to the single-mode core.

Even if, as described above, an angular deviation θi is applied to each of the elementary beams $B_{1i}$ at the proximal entrance of said twisted bundle of single-mode optical fibers, an angular deviation at the exit of the bundle of optical fibers is also observed due to the twist.

Figure 7A:
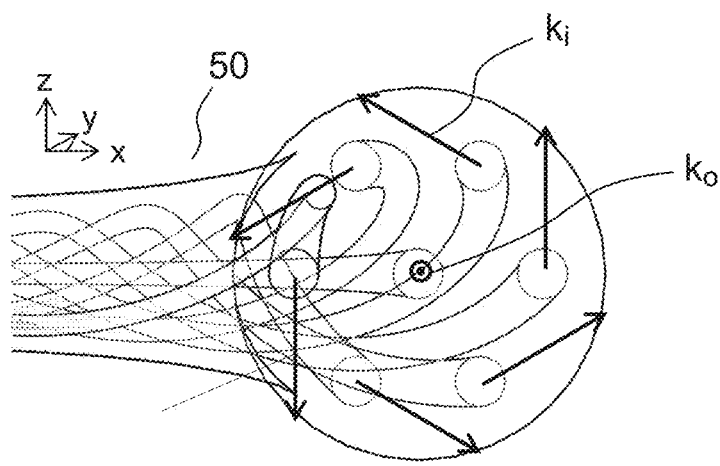
FIG. 7A, a schematic illustrating the angular deviation of a light beam output from each single-mode optical fiber of a twisted bundle of fibers.

FIG. 7A thus shows an exit face of the twisted MCF 50. The fundamental mode of the central core propagates parallel to the axis of the MCF; in other words its propagation vector $k_{(i=0)}$ (represented by a dot on the central fiber) is parallel to the axis of the MCF. The elementary beam that exits from the central core with the highest coupling efficiency is the one the propagation vector of which is equal to $k_0$, i.e. an elementary beam that also propagates parallel to the axis of the MCF. The situation is different for off-center cores: due to the helicity of these cores, the fundamental mode in these cores propagates at an angle with respect to the axis of the MCF; in other words, the propagation vector $k_i$ for an off-center core is not parallel to the axis of the MCF.

Figure 7B:
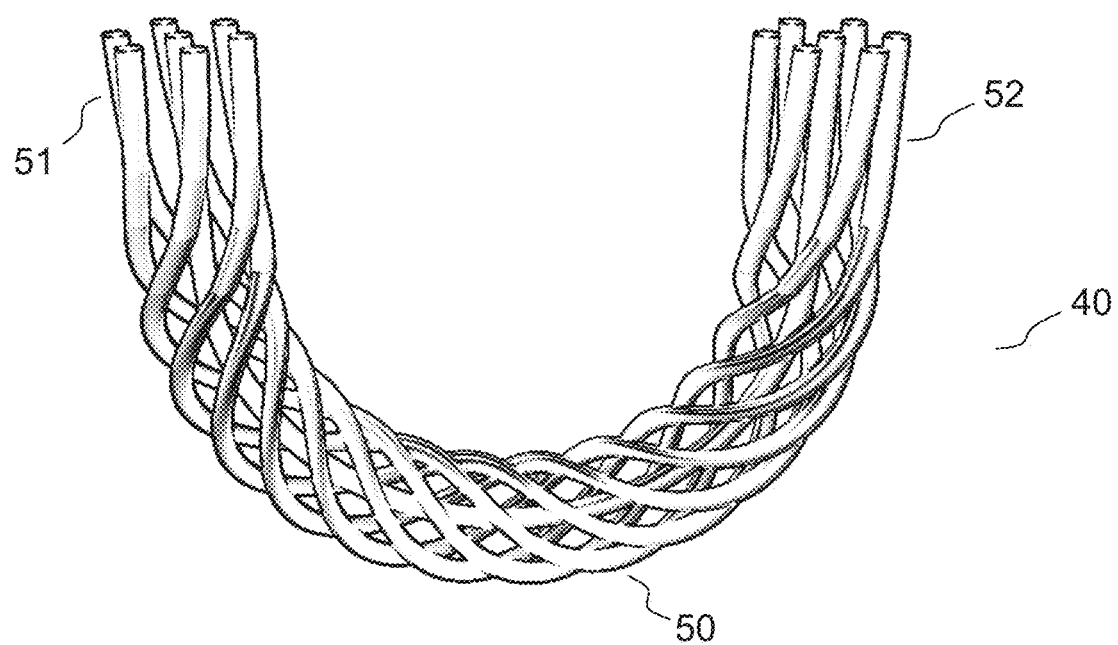
FIG. 7B, a schematic illustrating an example of a light guide according to the present description comprising a twisted bundle of single-mode optical fibers and, at its ends, a section of untwisted fibers.

One way to achieve optimal coupling at the distal and/or proximal end of the light guide is illustrated in FIG. 7B.

In this example, the light guide 40 comprises a twisted bundle 50 of single-mode optical fibers and, at the ends, sections of fibers, referenced 51 and 52, respectively, comprising a variation in the period of the twist that tends to infinity at the ends; in other words, at the interface of the section with free space, the single-mode optical fibers are parallel and the bundle of fibers is no longer twisted.

The applicants have shown that it is possible to produce an MCF comprising a short untwisted proximal section 51 that transforms into a long twisted section 50 that, ultimately, transforms into a short untwisted distal section 52. The transitions between twisted MCF and untwisted MCF are advantageously gradual, i.e. P increments or decrements continuously, this ensuring a transmission efficiency of 100% through the transition zone. See FIG. 7B. The untwisted sections in the distal and proximal portions for example have a length smaller than or equal to 1 cm.

The light guide shown in FIG. 7B may be manufactured by locally heating the MCF between two regions by virtue of a CO2 laser; when the glass has melted, a twist opposite to that of the MCF is applied; this results in an untwisted portion; the MCF is then cleaved in the location of the untwisted portion, this resulting in an untwisted end. The process is repeated for the other end of the MCF.

Figure 7C:
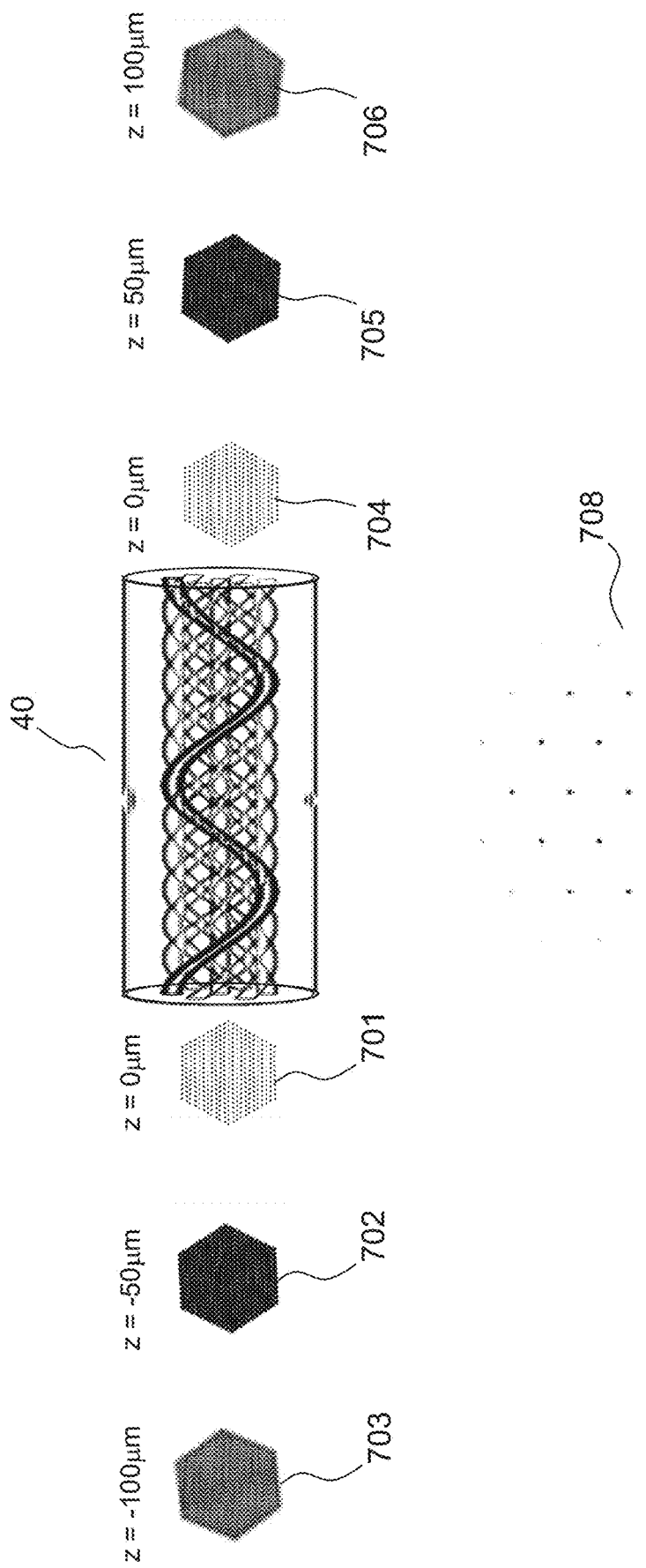
FIGS. 7C and 7D schematics illustrating patterns of the intensity of the electromagnetic field at various distances upstream and downstream of the twisted bundle of optical fibers in the case of a twisted bundle of optical fibers without untwisted sections (FIG. 7C) and with untwisted sections (FIG. 7D)
Figure 7D:
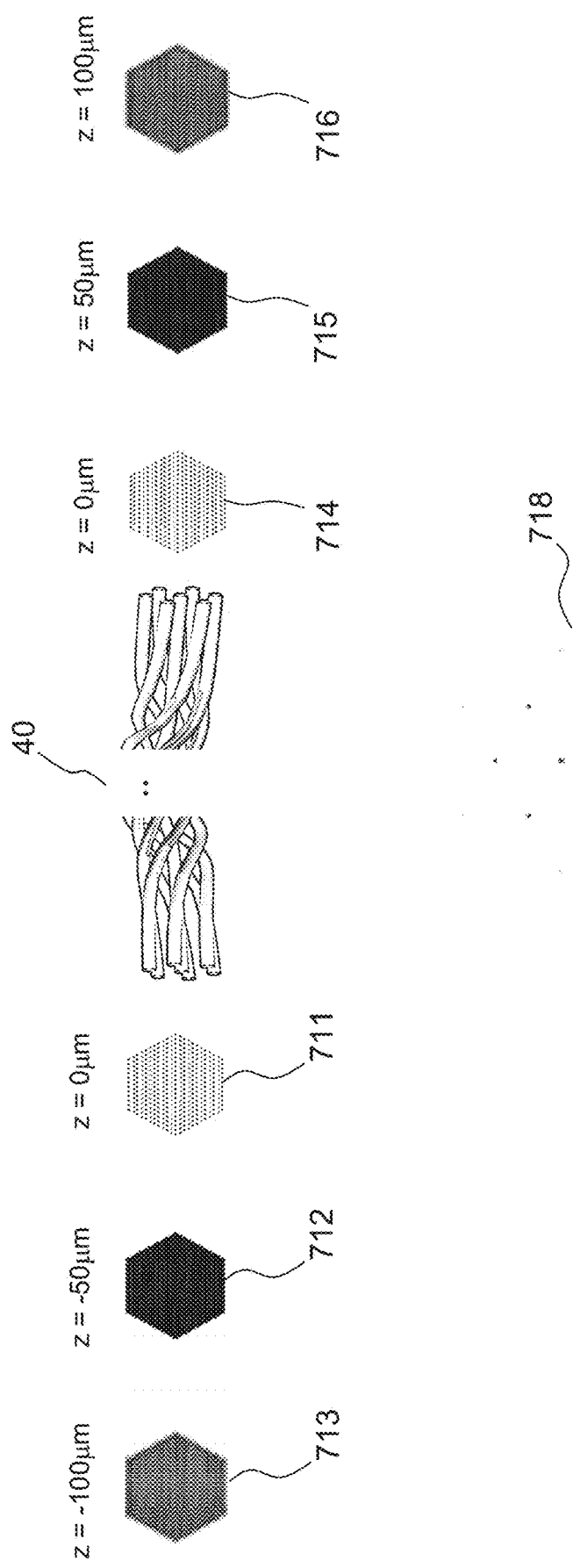

FIGS. 7C and 7D thus illustrate figures showing the intensity patterns of the electromagnetic field at various distances upstream and downstream of the twisted bundle of optical fibers in the case of a twisted bundle of optical fibers without untwisted sections (FIG. 7C) and with untwisted sections (FIG. 7D).

In the case of FIG. 7C, an application of angular deviations to each of the elementary beams at the proximal entrance of the twisted bundle of single-mode optical fibers, as described above, is assumed. The application of angular deviations may be seen in the intensity patterns 701 at the entrance face (z=0 µm) and in the intensity patterns 702, 703 at z=−50 µm and z=−100 µm, respectively, which show that the field has "rotated" to reach the entrance face. In other words, the field arrived at a given angle that is not perpendicular to the entrance face. This angle differs depending on the position of the core and its distance from the central core. Exit-side, due to the angular deviations undergone by the elementary beams propagating through the twisted bundle of optical fibers, it may be seen that the electromagnetic field rotates as it propagates (intensity patterns 704, 705, 706 corresponding to z=0 µm (exit face) z=50 µm and z=100 µm, respectively). This results in a poor overlap, in the far field, between the beams output from the single-mode cores, this leading to "spreading" (increase in the field of view) and to a decrease in the intensity of the central portion of the PSF (intensity pattern 708).

In the case of a light guide 40 comprising a bundle of twisted optical fibers and two sections in which the twist period varies in such a way as to obtain untwisted ends (FIG. 7D), it may be seen that the intensity pattern output from the guide (intensity patterns 714, 715, 716 corresponding to z=0 µm, z=50 µm and z=100 µm, respectively) remains stable and results in a PSF that is not spread, with a high intensity in the central portion (intensity pattern 718). Note that in the case of FIG. 7D an untwisted section was provided as entrance section of the bundle of fibers, this allowing the need to apply angular phase shifts to the elementary beams at the proximal entrance of the bundle of fibers to be avoided. This explains why the intensity patterns 711, 712, 713 corresponding to z=0 µm, z=−50 µm and z=−100 µm, respectively, are stable. It would have been possible to only provide an untwisted section as exit section of the bundle of fibers, and to apply angular phase shifts to the elementary beams at the proximal input of the bundle of fibers.

FIGS. 8A to 8D show comparative images obtained with a (completely twisted) bundle of fibers. The setup used to obtain the images is that shown in FIG. 2, with a detector arranged on the distal side of the bundle of optical fibers (images in transmission). Either a twisted fiber without curvature (801) or one with curvature (802) (FIG. 8A) was employed. The imaging was carried out according to the modality described above, i.e. the relative phase shifts of the various cores of an MCF were adjusted so as to obtain a focal point at the end of the MCF, then this focal point was swept over a sample. The sample here consisted of the number '5' selected from a negative USAF test chart (FIG. 8B) such that the image was reconstructed from the intensity transmitted for each point of the sample.

FIG. 8C shows an image obtained in transmission with the bundle of fibers for an almost linear position of the bundle of fibers (801, FIG. 8A) and for a curvature of 135° (802, FIG. 8A). The image is almost identical in both cases, this demonstrating that the focal point moves very little (by a distance smaller than one PSF or of the order of one PSF) in the field of view when the bundle of fibers is bent.

Figure 9:
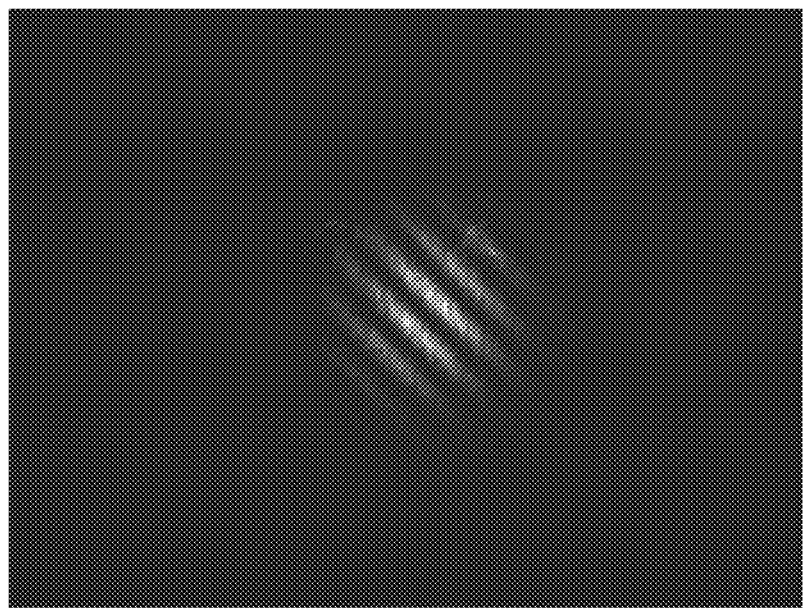
FIG. 9, an interference pattern allowing the preservation of phase between a peripheral fiber and a central fiber with a twisted fiber to be illustrated.

FIG. 9 illustrates an interference pattern illustrating the preservation of the phase between a peripheral fiber and a central fiber, with a twisted fiber.

More precisely, in order to evaluate the stability of the relative phase of the cores during bending for a twisted bundle of fibers, the applicants carried out interferometry experiments to examine interference between the light guided by the central core and the peripheral cores. When light is injected into the central fiber and into a peripheral fiber, inference fringes are obtained in the distal portion of the MCF that are characteristic of two-wave interference (FIG. 9). Noteworthily, this interference pattern does not change when the twisted bundle of fibers is bent.

The applicants have demonstrated that methods and devices according to the present description may also be employed in non-linear imaging to transport and control light beams, the device being suitable for the transmission of short pulses.

However, in the case of manipulation of ultra-short pulses, a group velocity delay (or GDD for "Group Delay Dispersion"), which is the delay undergone by light pulses traveling through the various cores of the bundle of fibers, is observed. There are two types of group velocity delay, the GDD referred to as 'static' GDD, which is associated with group velocity delays between cores for a linearly positioned fiber, this delay being related to variations in residual optical paths existing between the various cores of the bundle of fibers, and the GDD referred to as 'dynamic' GDD, which is associated with inter-core group velocity delay when the bundle of fibers is subjected to a curvature.

Figure 10A:
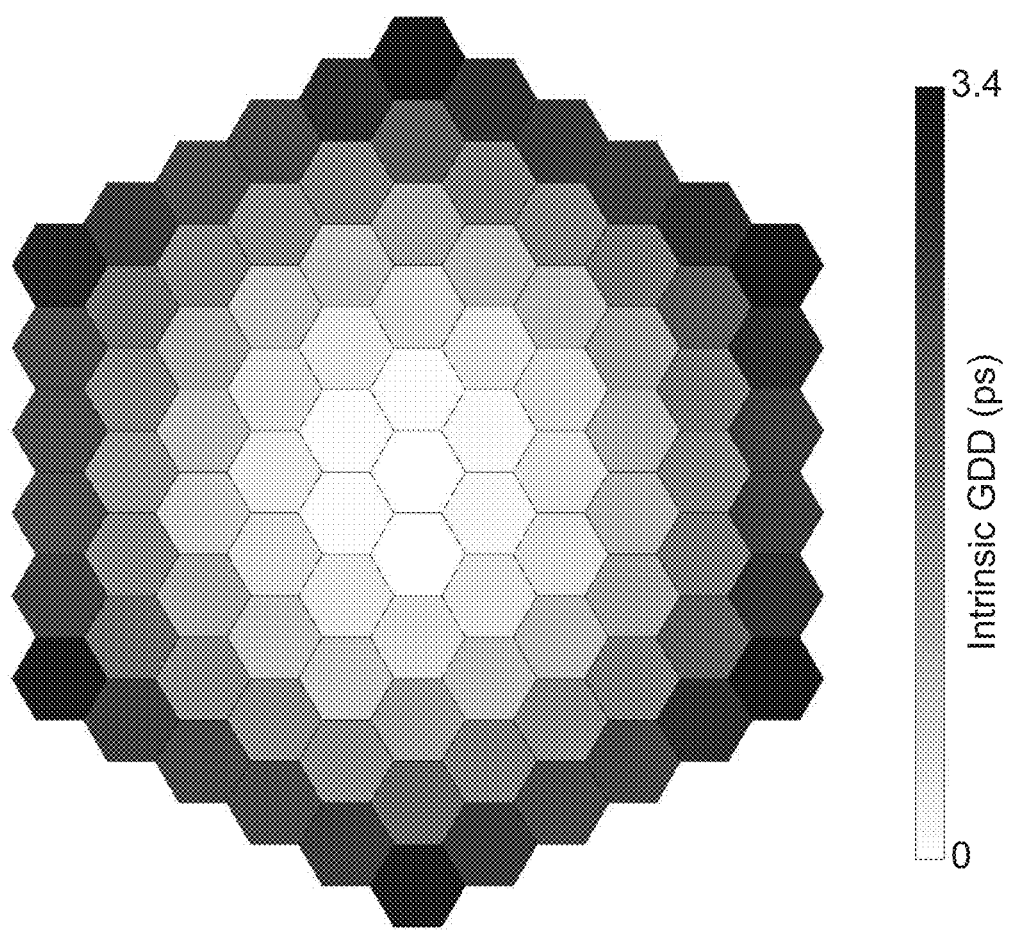
FIGS. 10A and 10B, schematics respectively illustrating intrinsic group delay (GDD) in a twisted bundle of single-mode optical fibers according to one example of the present description and the variation in the group delay between the twisted bundle of fibers when bent and unbent.

In the case of a bundle of fibers that is twisted as in the present description, the curvature generates an intrinsic GDD (illustrated in FIG. 10A).

More precisely, FIG. 10A illustrates the GDD measured for a twisted bundle of fibers with a length of 300 mm and a twist period P=8.2 mm, each hexagon representing a single core; the distance between the centers of adjacent hexagons is Λ=15.9 µm. Thus, only cores located within a radius of 5*15.9=80 µm from the center of the bundle of fibers have been shown. Each hexagon represents one core of the bundle of fibers and the GDD associated with that core. A high group velocity delay is observed with the twisted bundle of fibers. This is due to the difference in the effective lengths of the cores inside the bundle. The optical path of the central cores is short while it is much longer for the peripheral fibers, hence the optical-patch differences and therefore the observed GDD.

The GDD observed in FIG. 10A may be compensated by using a device for controlling the group velocity delay of the light pulses in the bundle of single-mode optical fibers (or GDC for "Group Delay Control"), as described in the publication of E. R. Andresen et al. ("*Measurement and compensation of residual group delay in a multi-core fiber for lensless endoscopy*", JOSA B, Vol. 32, No. 6, 1221-1228 (2015)).

It is also possible to compensate for the GDD observed in FIG. 10A using a bundle of fibers having cores the index of which varies as a function of the distance to the central core (lower index on the periphery) and/or by varying the size of the cores (smaller cores having lower propagation constants and therefore lower group delays).

Figure 10B:
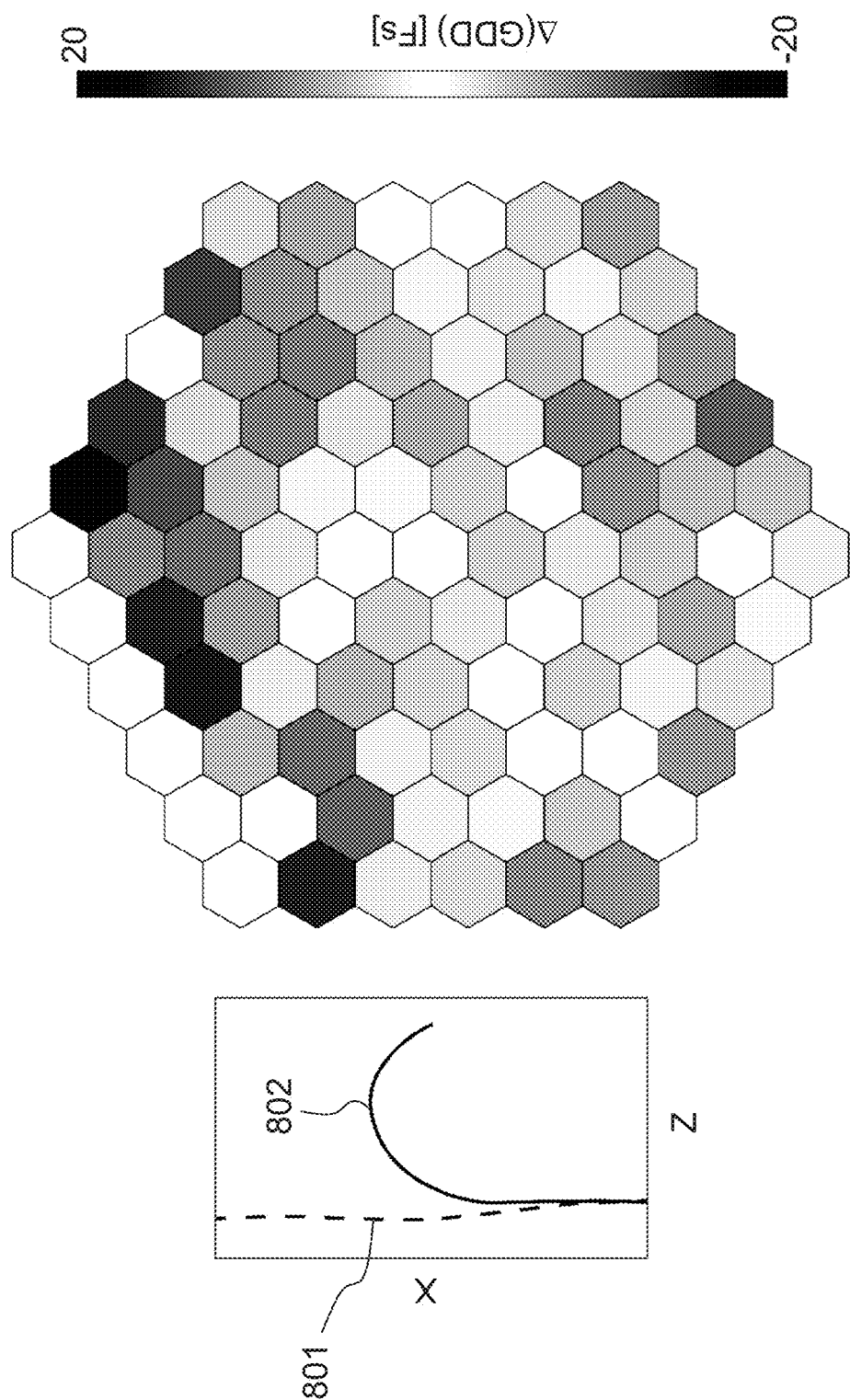

FIG. 10B illustrates the GDD difference measured between a fiber 801 without curvature and a bent fiber 802 with a curvature of 135° (corresponding to a radius of curvature of about 20 cm). It may be seen that the curvature does not cause GDD in the case of a MCF twisted according to the present description since the GDD difference is about 40 fs, i.e. much less than the duration of the laser pulses used, which is about 150 fs. Thus, when the twisted fiber is bent, the measured GDD remains constant and hence bending the MCF does not lead to additional GDD as is the case in untwisted and bent MCFs, such as described in "V. Tsvirkun et al., *"Bending-induced inter-core group delays in multicore fibers"* Optics Express 25, 31863-31875 (2017)".

Although described by way of a certain number of detailed exemplary embodiments, the device for transporting and controlling light beams comprises various variants, modifications and improvements that will appear obvious to those skilled in the art, it being understood that these various variants, modifications and improvements form part of the scope of the invention, such as defined by the following claims. In particular, the device for transporting and controlling light beams according to the present description is applicable to so-called "lensless" endomicroscopic imaging and to any other application based on using a bundle of uncoupled single-mode fibers to transport light beams and requiring the phase of the light beams at the exit of the bundle of single-mode optical fibers to be controlled.

The invention claimed is:

1. A device for transporting and controlling light beams, comprising:
    a light guide comprising a bundle of uncoupled single-mode optical fibers, each single-mode optical fiber being intended to receive an elementary light beam at a proximal end and to emit a light beam at a distal end, said bundle of single-mode optical fibers comprising, in operation, a minimum radius of curvature corresponding to a maximum curvature of the bundle of fibers;
    an optical device for phase controlling, said device being arranged on the side of the proximal end of the light guide and comprising:
        at least a first spatial light modulator suitable for applying a phase shift to each of the elementary beams;
        a control unit for controlling the first spatial light modulator, said control unit being configured to apply a phase shift to each of the elementary beams so as to form, at the distal end of the light guide, an illumination beam with a predefined phase function,
    and wherein said bundle of single-mode optical fibers is twisted, and comprises a twist period defined to preserve said phase function at the distal end of the light guide when the bundle of single-mode optical fibers is subjected to a curvature lower than said maximum curvature.

2. The device for transporting and controlling light beams as claimed in claim 1, wherein the twist period is comprised between 1 mm and 30 mm, and advantageously between 2.5 mm and 10 mm.

3. The device for transporting and controlling light beams as claimed in claim 1, wherein the length of the bundle of single-mode optical fibers is equal to k times the twist period where k is an integer.

4. The device for transporting and controlling light beams as claimed in claim 1, wherein the control unit for controlling the first spatial light modulator is furthermore configured to apply an angular deviation to each of the elementary beams at the proximal entrance of said twisted bundle of single-mode optical fibers, said angular deviation being defined, depending on the position of the single-mode fiber intended to receive said elementary beam in said bundle of single-mode optical fibers, so as to improve coupling to said single-mode fiber.

5. The device for transporting and controlling light beams as claimed in claim 1, wherein the light guide comprises at the distal end and/or at the proximal end of said twisted bundle of single-mode optical fibers a section of variable twist, wherein the twist period tends to infinity on the side of said distal and/or proximal end.

6. The device for transporting and controlling light beams as claimed in claim 5, wherein said section of variable twist has, at said distal and/or proximal end, an untwisted section having a length smaller than 1 cm.

7. The device for transporting and controlling light beams as claimed in claim 1, said device being suitable for transporting and controlling light beams comprising optical pulses, said device furthermore comprising a device for controlling the group velocity delays of the light pulses, the latter device being configured to suppress static group velocity delays between the single-mode fibers of said twisted bundle of single-mode optical fibers.

8. The device for transporting and controlling light beams as claimed in claim 1, wherein at least some of said single-mode optical fibers are doped.

9. An endomicroscopic imaging system comprising:
    a light source for emitting light beams;
    a device as claimed in claim 1, for transporting and controlling the light beams emitted by said source so as to form a beam for illuminating an object with a defined phase function; and
    a detection channel intended for the detection of the light returned by the object and transmitted through said at least one first light guide, from its distal end to its proximal end.

10. A method for transporting and controlling light beams, comprising:
    receiving elementary light beams at a proximal end of a bundle of N single-mode optical fibers of a light guide, wherein:
        each single-mode optical fiber is intended to receive an elementary light beam and to emit a light beam at a distal end;
        said bundle of single-mode optical fibers comprises, in operation, a minimum radius of curvature corresponding to a maximum curvature of the bundle of fibers; and
        said bundle of single-mode optical fibers is twisted, and comprises a twist period;
    applying, by means of at least a first spatial light modulator arranged on the side of the proximal end of said bundle of single-mode optical fibers, a phase shift to each of the elementary beams, in order to form, at the distal end of the light guide, an illumination beam with a defined phase function, said twist period being defined to preserve said phase function at the distal end of the light guide when the bundle of single-mode optical fibers is subjected to a curvature lower than said maximum curvature.

11. The method for transporting and controlling light beams as claimed in claim 10, furthermore comprising applying an angular deviation to each of the elementary light beams at the proximal entrance of said twisted bundle of single-mode optical fibers, said angular deviation being defined, depending on the position of the single-mode fiber intended to receive said elementary beam in said bundle of single-mode optical fibers, so as to improve coupling to said single-mode fiber.

12. The method for transporting and controlling light beams as claimed in claim 10, said method being suitable for transporting and controlling light beams comprising optical pulses, said method furthermore comprising suppressing static group velocity delays between the single-mode fibers of said twisted bundle of single-mode optical fibers by means of a device for controlling the group velocity delays of the light pulses.

13. The method for transporting and controlling light beams as claimed in claim 10, furthermore comprising a prior calibration allowing the phase shift to be applied to each of the elementary beams depending on the phase function sought for the illumination beam to be determined.

14. An endomicroscopic imaging method employing no lens distal side, comprising:
- emitting light beams;
- transporting and controlling the light beams by means of a method as claimed in claim 10 so as to illuminate an object with said illumination beam;
- detecting the light returned by the object and transmitted through the light guide, from its distal end to its proximal end.

* * * * *